(12) United States Patent
Peterfreund et al.

(10) Patent No.: US 9,764,087 B2
(45) Date of Patent: Sep. 19, 2017

(54) PREDICTION, VISUALIZATION, AND CONTROL OF DRUG DELIVERY BY INFUSION PUMPS

(71) Applicant: The General Hospital Corporation, Boston, MA (US)

(72) Inventors: Robert A. Peterfreund, Newtonville, MA (US); Michael Parker, Newton, MA (US); Nathaniel M. Sims, Milton, MA (US); Mark A. Lovich, Brookline, MA (US); Harold J. DeMonaco, Salem, MA (US)

(73) Assignees: The General Hospital Corporation, Boston, MA (US); Steward St. Elizabeth's Medical Center of Boston, Inc., Boston, MA (US)

( * ) Notice: Subject to any disclaimer, the term of this patent is extended or adjusted under 35 U.S.C. 154(b) by 0 days.

(21) Appl. No.: 14/360,226

(22) PCT Filed: Nov. 20, 2012

(86) PCT No.: PCT/US2012/066019
§ 371 (c)(1),
(2) Date: May 22, 2014

(87) PCT Pub. No.: WO2013/078179
PCT Pub. Date: May 30, 2013

(65) Prior Publication Data
US 2014/0303591 A1    Oct. 9, 2014

Related U.S. Application Data

(60) Provisional application No. 61/563,418, filed on Nov. 23, 2011.

(51) Int. Cl.
*A61M 5/168* (2006.01)
*A61M 5/142* (2006.01)
*G06F 19/00* (2011.01)

(52) U.S. Cl.
CPC ........ *A61M 5/16827* (2013.01); *A61M 5/142* (2013.01); *G06F 19/3468* (2013.01);
(Continued)

(58) Field of Classification Search
CPC .......... A61M 5/16827; A61M 5/16877; A61M 2005/1402; A61M 5/168; A61M 5/142;
(Continued)

(56) References Cited

U.S. PATENT DOCUMENTS 5,240,035 A    8/1993 Aslanian et al.
5,681,285 A    10/1997 Ford et al.
(Continued)

FOREIGN PATENT DOCUMENTS

JP    H01-265973    10/1989
JP    2004-000495    1/2004
(Continued)

OTHER PUBLICATIONS

International Search Report and Written Opinion mailed Mar. 6, 2013 in international application No. PCT/US2012/066019, 11 pgs.
(Continued)

*Primary Examiner* — Imani Hayman
*Assistant Examiner* — Nilay Shah
(74) *Attorney, Agent, or Firm* — Fish & Richardson P.C.

(57) ABSTRACT

Systems for predicting a drug delivery profile as described herein include at least one drug pump and/or a controllable valve that produce a drug flow and dispense at least a first drug. The system also includes at least one carrier fluid pump and/or another controllable valve that produces a carrier fluid flow, a flow junction structure configured to
(Continued)

receive the drug flow and the carrier fluid flow to produce a mixed flow, and a fluid path for carrying the mixed flow between the flow junction structure and a delivery point. The system further includes a processing device configured to predict the drug delivery profile at the delivery point based on determining a predicted time variation of drug concentration at the delivery point using at least a model of the mixed flow. The model includes a plurality of parameters related to propagation of the mixed flow through the fluid path.

13 Claims, 12 Drawing Sheets

(52) U.S. Cl.
CPC ............... *A61M 5/16877* (2013.01); *A61M 2005/14292* (2013.01); *G06F 19/3437* (2013.01)

(58) Field of Classification Search
CPC .......... A61M 5/16804; A61M 5/16813; A61M 5/172; A61M 5/1408; A61M 5/1409
See application file for complete search history.

(56) References Cited

U.S. PATENT DOCUMENTS

| | | | |
|---|---|---|---|
| 6,129,702 | A | 10/2000 | Woias et al. |
| 6,279,869 | B1 | 8/2001 | Olewicz |
| 6,491,666 | B1 | 12/2002 | Santini, Jr. et al. |
| 7,347,854 | B2* | 3/2008 | Shelton et al. ............ 604/891.1 |
| 7,887,520 | B2 | 2/2011 | Simon |
| 2002/0169636 | A1 | 11/2002 | Eggers et al. |
| 2003/0130617 | A1 | 7/2003 | Leone |
| 2003/0171738 | A1 | 9/2003 | Konieczynski et al. |
| 2004/0082920 | A1* | 4/2004 | Mori et al. ................ 604/246 |
| 2004/0103897 | A1* | 6/2004 | Hickle ................ G06F 19/3468 128/204.23 |
| 2004/0171983 | A1* | 9/2004 | Sparks .............. A61M 5/16827 604/65 |
| 2005/0059926 | A1* | 3/2005 | Sage, Jr. ............... A61M 5/168 604/65 |
| 2005/0070875 | A1* | 3/2005 | Kulessa ...................... 604/500 |
| 2005/0277912 | A1* | 12/2005 | John .......................... 604/890.1 |
| 2007/0255135 | A1 | 11/2007 | Kalafut et al. |
| 2008/0125759 | A1 | 5/2008 | Konieczynski et al. |
| 2009/0177188 | A1 | 7/2009 | Steinkogler |
| 2009/0306592 | A1 | 12/2009 | Kasai et al. |
| 2010/0318025 | A1* | 12/2010 | John ................ A61M 25/0026 604/84 |
| 2011/0270188 | A1 | 11/2011 | Caffey et al. |
| 2013/0053823 | A1 | 2/2013 | Fiering et al. |
| 2013/0218080 | A1 | 8/2013 | Peterfreund et al. |

FOREIGN PATENT DOCUMENTS

| | | |
|---|---|---|
| JP | 2005-506103 | 3/2005 |
| JP | 2008/540004 | 11/2008 |
| WO | WO 02/069099 | 9/2002 |
| WO | WO 2005/007223 | 1/2005 |
| WO | WO2006/112903 | 10/2006 |
| WO | WO 2009/149367 | 12/2009 |

OTHER PUBLICATIONS

International Search Report and Written Opinion mailed Feb. 9, 2012 in International Application No. PCT/US2011/037734, 10 pgs.
International Preliminary Report on Patentability in International Application No. PCT/US2011/037734, Dec. 6, 2012, 6 pages.
International Preliminary Report on Patentability in International Application No. PCT/US2012/066019, issued May 27, 2014, 8 pages.
Bartels et al., "An Analysis of Drug Delivery Dynamics via a Pediatric Central Venous Infusion System: Quantification of Delays in Achieving Intended Doses," Anesth Analg., Oct. 2009, 109(4):1156-1161.
Levi et al., "Connecting multiple low-flow intravenous infusions in the newborn: Problems and possible solutions," Pediatr Crit Care Med., 2010, 11(2):275-281.
Lovich et al., "Central venous catheter infusions: A laboratory model shows large differences in drug delivery dynamics related to catheter dead volume," Crit Care Med., 2007, 35(12):2792-2798.
Lovich et al., "The Delivery of Drugs to Patients by Continuous Intravenous Infusion: Modeling Predicts Potential Dose Fluctuations Depending on Flow Rates and Infusion System Dead Volume," Aneth Analg., 2006, 102:1147-53.
Lovich et al., "The Impact of Carrier Flow Rate and Infusion Set Dead-Volume on the Dynamics of Intravenous Drug Delivery," Anesth Analg., 2005, 100:1048-55.
Ma et al., "Quantitative analysis of continuous intravenous infusions in pediatric anesthesia: safety implications of dead volume, flow rates, and fluid delivery," Pediatric Anesth., 2011, 21:78-86.
Moss et al., "An In Vitro Analysis of Central Venous Drug Delivery by Continuous Infusion: The Effect of Manifold Design and Port Selection," Aneth Anal., Nov. 2009, 109(5):1524-1529.
Neff et al., "Flow rate, syringe size and architecture are critical to start-up performance of syringe pumps," EP J Anesth., 2007, 24:602-608.
Nunnally, "Sports cars versus freight trains: Why infusion performance is in the details," Crit Care Med., 2007, 35(12):2872-2873.
International Search Report and Written Opinion in International Application No. PCT/US2015/030732, dated Aug. 7, 2015, 13 pages.
Mexican Office Action issued in Mexican Application No. MX/a/2014/006250, dated Dec. 11, 2015, 5 pages (with English translation).
European Office Action issued in European Application No. EP11787242.4, dated Oct. 21, 2015, 6 pages.
European Office Action issued in European Application No. EP12851614, dated Jul. 28, 2015, 7 pages.
Supplemental European Search Report issued in European Application No. EP11787242.4, dated Sep. 30, 2015, 5 pages.
European Search Report issued in EP12851614 on Jul. 17, 2015 (3 pages).
Office Action issued in MX/a/2014/006250 on Jul. 24, 2015 (7 pages).
Mexican Office Action issued in Mexican Application No. MX/a/2014/006250, dated Mar. 23, 2016, 7 pages.
European Office Action in European Application No. 11787242.4, dated Oct. 18, 2016, 4 pages.
International Preliminary Report on Patentability in International Application No. PCT/US2015/030732, mailed on Nov. 24, 2016, 8 pages.
Japanese Office Action in Japanese Application No. 2014-543529, dated Nov. 8, 2016, 14 pages (with English translation).
US Non-Final Office Action in U.S. Appl. No. 13/698,110, dated Sep. 13, 2016, 29 pages.

* cited by examiner

US 9,764,087 B2

PREDICTION, VISUALIZATION, AND CONTROL OF DRUG DELIVERY BY INFUSION PUMPS

PRIORITY CLAIM

This application is a 35 U.S.C. §371 national stage application of International Application No. PCT/US2012/066019, filed Nov. 20, 2012, which claims the benefit of U.S. Provisional Patent Application No. 61/563,418, filed Nov. 23, 2011. The entire contents of the foregoing applications are incorporated herein by reference.

TECHNICAL FIELD

The present disclosure relates to control systems for infusion pumps.

BACKGROUND

A drug infusion system used for administering a drug to a patient typically includes a pump for dispensing the drug and another pump for dispensing a carrier fluid. The drug and the carrier fluid are mixed together at a junction such as a manifold and transported to the patient via a fluid path. The volume of the fluid path is referred to as "dead volume" (sometimes referred to as "dead space") and constitutes a space traversed by the fluid before the drug can reach the patient. The dead volume can cause a considerable discordance between an intended delivery profile and an actual delivery profile of drug delivered to the patient. Such discordance can cause a delay in delivering an intended dose of drug to the patient at a desired time.

SUMMARY

The present disclosure features methods and systems for controlling one or more infusion pumps such that an actual delivery profile of one or more drugs can be controlled. A delivery profile, as used in this application, refers to a rate of drug delivery at a delivery point over a range of time. The present disclosure also features controllable valves that can be used either independently or in conjunction with the one or more infusion pumps to control the delivery profile of one or more drugs. The methods and systems described herein are based on algorithms, some of which depend on predicatively modeling the flow of the one or more drugs and the carrier fluid in at least portions of a fluid path between the pumps and a delivery point. Predictive models can take into consideration multiple physical parameters including radial diffusion (molecules moving toward the walls of the tubing or catheter), axial diffusion (molecules moving along the axis of flow), laminar flow (smooth bulk fluid flow), physical chemical properties of the particular drug, and the interactions thereof and can therefore be more accurate than empirical models derived primarily through back fitting of data. Output of the infusion pumps and/or controllable valves can be adjusted based on delivery profiles computed using one or more of the predictive models.

In one aspect, systems for predicting one or more drug delivery profiles include at least one drug pump that produces a drug flow. The drug pump dispenses at least a first drug. The systems also include at least one carrier fluid pump that produces a carrier fluid flow, a flow junction structure configured to receive the drug flow and the carrier fluid flow to produce a mixed flow, and a fluid path for carrying the mixed flow between the flow junction structure and a delivery point. The systems further include a processing device configured to predict the drug delivery profile at the delivery point based on determining a predicted time variation of drug concentration at the delivery point using at least a model of the mixed flow. The model includes a plurality of parameters related to propagation of the mixed flow through the fluid path.

In another aspect, methods for predicting a delivery rate of a drug at a delivery point include receiving, at a processing device, one or more operating parameters related to a drug pump that dispenses a drug and a carrier fluid pump that dispenses a carrier fluid. The methods also include determining, by the processing device, a delivery rate of the drug at the delivery point by predicting time variation of a concentration of the drug at the delivery point based at least on a mathematical model of a mixed flow through a fluid path that terminates at the delivery point. The mixed flow includes the drug and the carrier fluid, and the model includes the one or more operating parameters and a plurality of flow-parameters related to the mathematical model of the mixed flow.

In another aspect, systems for controlling a drug delivery profile include at least one drug pump that produces a drug flow and at least one carrier fluid pump that produces a carrier fluid flow. The drug pump dispenses at least a first drug. The systems also include a flow junction structure configured to receive the drug flow and the carrier fluid flow to produce a mixed flow, and a fluid path for carrying the mixed flow between the flow junction structure and a delivery point. The systems further include a control module configured to control the drug delivery profile at the delivery point by controlling a drug flow rate and a carrier fluid flow rate such that a ratio between the drug flow rate and the carrier fluid flow rate is substantially fixed over a range of time. The mixed flow is varied to achieve a particular drug delivery profile.

In another aspect, methods for controlling a drug delivery profile include receiving, at a processing device, information on a drug flow rate related to a drug pump that dispenses a drug and information on a carrier fluid flow rate related to a carrier fluid pump that dispenses a carrier fluid. The methods also include controlling, by a control module, the drug delivery profile at the delivery point by adjusting the drug flow rate and the carrier fluid flow rate such that a ratio between the drug flow rate and the carrier fluid flow rate is substantially fixed over a range of time.

In another aspect, methods for predicting a delivery rate of a drug at a delivery point include receiving, at a processing device, one or more operating parameters related to a first container that dispenses a drug and a second container that dispenses a carrier fluid, both at a constant predefined pressure. The predefined pressure can be regulated by an inline pressure control valve or a constant force such as gravity. The methods also include determining, by the processing device, a delivery rate of the drug at the delivery point by predicting time variation of a concentration of the drug at the delivery point based at least on a mathematical model of a mixed flow through a fluid path that terminates at the delivery point. The mixed flow includes the drug and the carrier fluid, and the model includes the one or more operating parameters and a plurality of flow-parameters related to the mathematical model of the mixed flow.

In another aspect, systems for controlling a drug delivery profile include a first controllable valve that produces a drug flow and a second controllable valve that controls a carrier fluid flow. The systems also include a flow junction structure configured to receive the drug flow and the carrier fluid flow to produce a mixed flow, and a fluid path for carrying the mixed flow between the flow junction structure and a delivery point. The systems further include a control module configured to control the drug delivery profile at the delivery point by controlling the resistance to flow under constant pressure carrier fluid flow rate such that a ratio between the drug flow rate and the carrier fluid flow rate is substantially fixed over a range of time. The mixed flow is varied to achieve a particular drug delivery profile.

In another aspect, computer readable storage devices have encoded thereon instructions that, when executed, cause a processor to receive one or more operating parameters related to a drug pump that dispenses the drug and a carrier fluid pump that dispenses a carrier fluid. The instructions further cause a processor to determine a delivery rate of the drug at the delivery point by predicting time variation of a concentration of the drug at the delivery point based at least on a mathematical model of a mixed flow through a fluid path that terminates at the delivery point. The mixed flow includes the drug and the carrier fluid, and the model includes the one or more operating parameters and a plurality of flow-parameters related to the mathematical model of the mixed flow.

In another aspect, computer readable storage devices have encoded thereon instructions that, when executed, cause a processor to receive information on a drug flow rate related to a drug pump that dispenses a drug and information on a carrier fluid flow rate related to a carrier fluid pump that dispenses a carrier fluid. The instructions further cause a processor to control a drug delivery profile at a delivery point by controlling the drug flow rate and the carrier fluid flow rate such that a ratio between the drug flow rate and the carrier fluid flow rate is substantially fixed over a range of time.

Implementations can include one or more of the following aspects, individually or in combination. For example, various implementations can include combinations and subcombinations of two or more of the following features.

A control module can be configured to control the drug flow and the carrier fluid flow such that a particular drug delivery profile is achieved at a future time point. The control module can be further configured to compute a rate of the drug flow and a rate of the carrier fluid flow at a given time point such that the particular drug delivery profile is achieved at the future time point. A display device can display data on the predicted drug delivery profile. At least one alarm can be configured to be triggered on detecting that at least one of i) a current drug flow rate, ii) a current carrier fluid rate or iii) a predicted drug delivery profile is outside a corresponding pre-defined desired or safe range associated with the drug. The safe range associated with the drug can be retrieved from a database. At least one sensor can be configured to provide data on a flow rate of the mixed flow at a particular portion of the delivery path. The control module can be configured to control the drug flow and the carrier fluid flow such that a proportion of the drug and the carrier fluid in the mixed flow, over a given portion of the fluid path, are substantially fixed. The processing device can be further configured to predict the drug delivery profile at the delivery point based also on user-input parameters on the drug flow and the carrier flow.

The parameters related to propagation of the mixed flow through the fluid path can include parameters characterizing one or more of i) radial diffusion, ii) axial diffusion, iii) laminar flow through the fluid path or iv) a physical or chemical property of the drug. In some implementations, the parameters related to propagation of the mixed flow through the fluid path can consist of a combination of two or more parameters characterizing i) radial diffusion, ii) axial diffusion, iii) laminar flow through the fluid path and iv) a physical or chemical property of the drug. The model can include structural parameters representing characteristics of at least one of the drug pump, the carrier fluid pump, the flow junction structure, or the fluid path. In some implementations, the model can consist of a combination of two or more structural parameters representing characteristics of the drug pump, the carrier fluid pump, the flow junction structure, and the fluid path. The structural parameters can include a dead volume associated with the fluid path. The dead volume can be empirically determined by examining a series of candidate empirical dead volumes and selecting one that best fits a control curve in a least squares sense. The processing device can be further configured to access a storage device that stores the structural parameters.

The processing device can be configured to identify at least one of the drug pumps, the carrier fluid pump, the flow junction structure, and the fluid path based on an identifier. The identifier can be a radio frequency identification (RFID) tag or a barcode and the processing device is coupled to an RFID tag reader or a barcode reader.

At least one additional drug pump can dispense at least a second drug and the control module can be configured to control the second drug flow such that a particular delivery profile of the second drug is achieved at the future time point. At least one of the drug pump or the carrier fluid pump can be a syringe pump or an infusion pump. A display device can display data on predicted drug delivery profiles of the first and second drugs.

The control module can be further configured to adjust a drug delivery rate at the delivery point within the range of time by simultaneously controlling the drug flow rate and the carrier fluid flow rate. A drug concentration in the drug flow can be substantially fixed over the range of time. The control module can adjust the drug delivery rate to achieve a predicted drug delivery rate calculated using at least a model of the mixed flow. The control module can be further configured to adjust the drug delivery profile such that excess volume delivery over time is substantially reduced while maintaining target drug delivery within allowable tolerances. The model can include a plurality of parameters related to propagation of the mixed flow through the fluid path.

The control module can be further configured to set an initial drug flow rate and an initial carrier fluid flow rate at substantially high values within corresponding allowable ranges at an onset of the range of time, and reduce, after a predetermined amount of time has elapsed, the drug flow rate and the carrier fluid flow rate such that the drug delivery profile can be achieved at the delivery point. The predetermined amount of time can be substantially equal to a time taken by the mixed flow to traverse the fluid path when the drug flow rate and the carrier fluid flow rate are set at the initial drug flow rate and the initial carrier fluid flow rate, respectively. At least one controllable valve can be disposed upstream from the flow junction structure, wherein the control module controls the drug delivery profile at the delivery point by controlling a flow through the controllable valve. A constant pressure valve can be disposed upstream from the controllable valve, wherein the constant pressure valve is configured to maintain a constant pressure upstream of the controllable valve for a fluid that flows through the controllable valve.

The methods and systems described herein provide numerous benefits and advantages (some of which may be achieved only in some of its various aspects and implementations) including the following. In general, controlling the one or more drug pumps and the carrier fluid pump in conjunction with one another, using algorithms based in part on a mathematical model, facilitates accurate control over changes in drug delivery at the delivery point. For example, the models described herein can be used to predict when and how the output profile at a drug infusion pump has to be changed such that a particular delivery profile is achieved at the delivery point. The delay between an activation of a drug infusion pump and the time when the appropriate amount of drug actually reaches the delivery point can be reduced significantly, thereby facilitating quick drug delivery especially in critical care settings. Accurate control over drug delivery profiles, as well as warning systems for detecting dangerous conditions, avoid potentially life threatening drug delivery variations and make the drug infusion pumps much more reliable and safe. In addition, accurate control also enables the ability to minimize the delivered volume of fluid, an important consideration when delivering infused medications to patients with compromised organ function. The methods and systems described herein can also be used to predict drug delivery profiles at the delivery point and trigger alarms if the predicted delivery profile lies outside an allowable or safe range. By using one or more resistance valves, the resistance of which can be controlled substantially continuously or continuously, the flow can be controlled in accordance with desired settings under substantially constant upstream pressure.

Unless otherwise defined, all technical and scientific terms used herein have the same meaning as commonly understood by one of ordinary skill in the art. Although methods and materials similar or equivalent to those described herein can be used, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The inventions described herein can be implemented in many ways. Some useful implementations are described below. The descriptions of implementations of the inventions are not descriptions of the inventions, which are not limited to the detailed implementations described in this section, but are described in broader terms in the claims.

System Overview

Figure 1A:
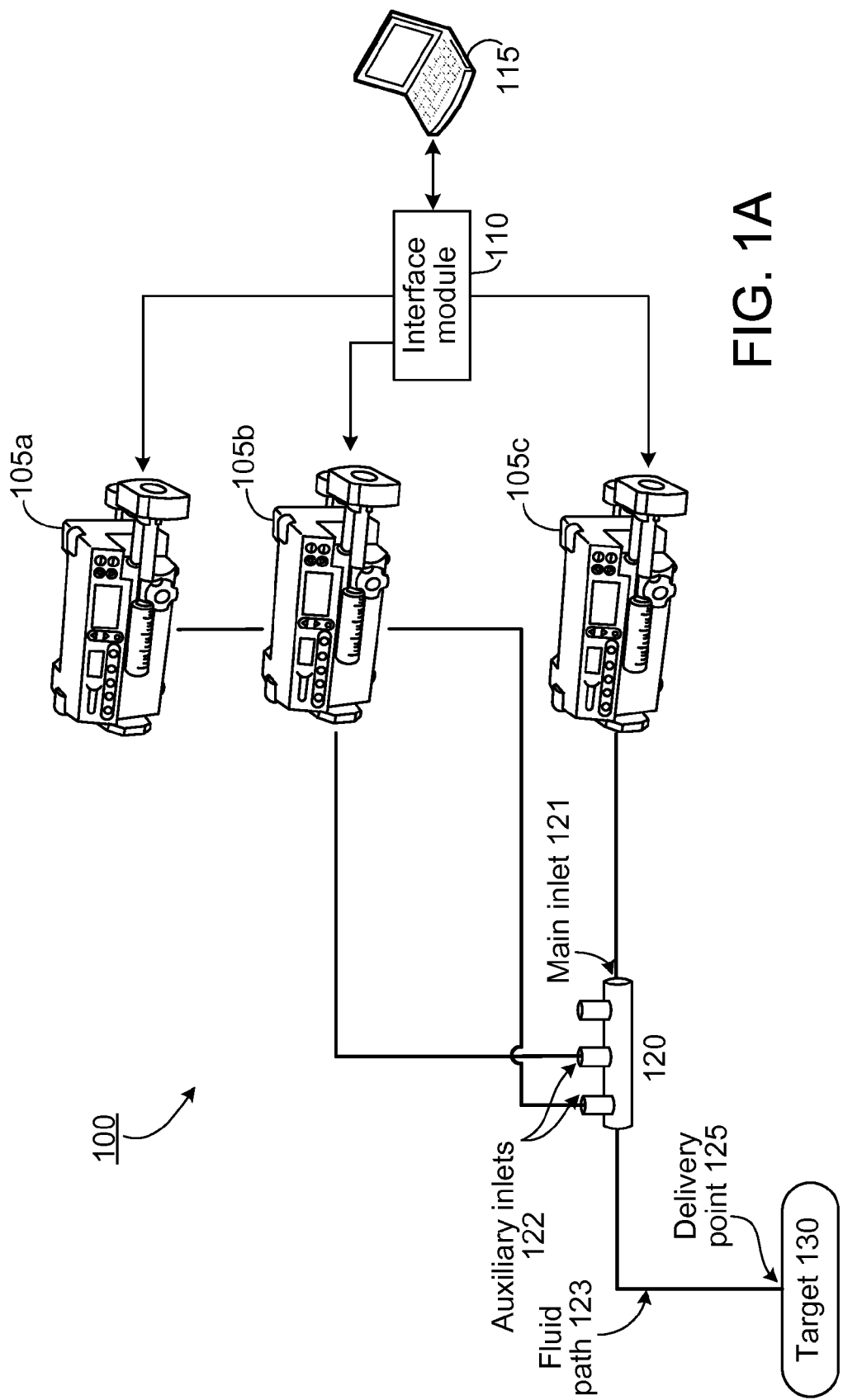
FIG. 1A is a schematic block diagram of an example of a system for controlling fluid delivery.

FIG. 1A shows a schematic block diagram of an example of a system 100 for controlling fluid delivery, e.g., in infusion pump systems. The system 100 includes multiple infusion pumps 105a, 105b and 105c (105, in general) that deliver fluids (e.g. drugs and carrier fluids) to a target 130. The fluids from the multiple infusion pumps 105 are mixed with each other at a flow junction structure 120 and transported over a fluid path 123 and delivered to the target 130 at a delivery point 125. The fluid outputs of infusion pumps 105 can be controlled by a computing device 115, possibly in communication with an interface module 110. Even though the interface module 110 is shown as a separate unit in FIG. 1A, in some implementations, the interface module 110 may reside on an infusion pump 105 or computing device 115.

The drugs delivered by the infusion pumps 105 can include any compound or composition that can be administered at the target in a liquid form. For example, drugs can include medicines, nutrients, vitamins, hormones, tracer dies, pharmaceutical compounds, chemicals, or any other substance delivered at the target for preventive, therapeutic, or diagnostic reasons. The target 130 can include any living being, for example a human patient, an animal, or a plant. In some implementations, the target 130 can also include nonliving articles such as an apparatus (e.g., a reaction chamber) where a fluid mixture is to be delivered in a controlled fashion.

The infusion pump 105 is typically used for introducing fluids, for example the drugs mentioned above, at a portion of the target. For example the infusion pump 105 can be used to introduce drugs into a patient's circulatory system. In general, the infusion pump 105 administers a controlled amount of a fluid over a period of time. In some implementations, the infusion pump 105 dispenses the fluid at a continuous flow rate. In some implementations, the infusion pump 105 dispenses a predetermined amount of fluid repeatedly after predetermined time intervals. For example, the infusion pump 105 can be configured to dispense 0.1 ml of a given drug every hour, every minute, etc. In some implementations the infusion pump 105 can be configured to dispense a fluid on demand, for example as directed by a healthcare personnel or even a patient. In such cases, the infusion pump 105 can also include overdose protection systems to protect against dispensing potentially hazardous amounts. For example, the infusion pump 105 can be a "smart pump" that is equipped with safety features (e.g. alarms and pre-emptive shutdown) that activate when there is a risk of an adverse drug interaction, or when an operator sets the pumps' parameters outside of specified safety limits.

The infusion pump 105 can operate in various ways. For example the infusion pump 105 can be a syringe pump where the fluid is held in the reservoir of a syringe, and a movable piston controls dispensing of the fluid. In some implementations, the infusion pump 105 can be an elastomeric pump where the fluid is held in the stretchable balloon reservoir, and pressure from elastic walls of the balloon dispenses the fluid. The infusion pump 105 can also include a peristaltic pump where a set of rollers presses down on a length of flexible tubing thereby dispensing the fluid through the tubing. Other propulsion mechanisms may be used in some implementations of pump systems. The infusion pump 105 can also be a multichannel pump where fluids are dispensed from multiple reservoirs, possibly at different rates.

The infusion pump 105 can also include one or more ports to receive a control signal that controls a fluid output from the infusion pump. For example, the infusion pump 105 can include a Universal Serial Bus (USB) port for receiving control signals for an actuator that regulates the pressure controlling the fluid output. In some implementations, the infusion pump 105 can feature a wireless receiver (for example a Bluetooth receiver, an infrared receiver, etc.) for receiving the control signal. In some implementations, the infusion pump 105 may be Wi-Fi enabled such that the infusion pump can receive the control signal over a wireless network such as a wireless local area network (WLAN). In some implementations, the infusion pump 105 may be configured to receive the control signal over any combination of wired and wireless networks.

In some implementations, one of the infusion pumps (for example the infusion pump 105c) dispenses a carrier fluid that is mixed with the drugs (dispensed from one or more other infusion pumps) at a flow junction structure, and the mixed fluid is delivered to the target. In general, the amount of volume from drugs that are delivered is small and therefore the carrier fluid constitutes a significant portion of the fluid that is delivered to the target. Various substances such as polymeric materials can be used as the carrier fluid. Some characteristics of the carrier fluid can include an adequate drug-loading capacity, water solubility when drug-loaded, a suitable molecule or weight range, a stable carrier-drug linkage in body fluids, biodegradability, non-toxicity, and general biocompatibility. In some implementations, the carrier fluid may also be desired to be non-immunogenic. Carrier fluids can transport drugs in various ways. In some implementations the carrier fluid acts as a matrix and the drug is carried uniformly distributed throughout the matrix. In some implementations the carrier fluid acts as a solvent and the drug is dissolved within the carrier fluid. In some implementations the drug can also be chemically or magnetically linked with molecules of the carrier fluid. Various polymeric materials, e.g., soluble polymers, biodegradable or bioerodable polymers, and mucoadhesive polymers, can be used as the carrier fluid. Typical carrier fluids in common clinical use can include 0.9% sodium chloride (Normal Saline) and Dextrose 5% in water (D5W) although other carrier fluids can be employed in some implementations.

Even though FIG. 1A shows only two infusion pumps 105a and 105b for dispensing drugs and only one infusion pump 105c for dispensing the carrier fluid, higher or lower numbers of infusion pumps are also possible. For example, a system may feature only a single infusion pump for dispensing a drug and a single infusion pump for dispensing the carrier fluid. In some implementations, a higher number of infusion pumps (e.g., three or four or even more) can be used for dispensing multiple drugs. In some implementations multiple infusion pumps can be used for dispensing two or more different types of carrier fluid.

In general, the carrier fluid dispensed from the infusion pump 105c and the one or more drugs dispensed from the other infusion pumps (e.g. 105a and 105b) are mixed together at the flow junction structure 120. In some implementations the flow junction structure 120 is a manifold with one main inlet 121 for accommodating the carrier fluid flow and multiple auxiliary inlets 122 for accommodating the drug flows. The shape, size, and number of inlets of the flow junction structure 120 can depend on the number of infusion pumps 105 used in the system. The flow junction structure 120 shown in FIG. 1A features two occupied auxiliary inlets for accommodating drugs dispensed from the infusion pumps 105a and 105b and one main inlet 121 for accommodating the carrier fluid dispensed from the infusion pump 105c. However, for higher number of infusion pumps, the flow junction structure 120 can have additional main inlets 121 and/or auxiliary inlets 122 as needed. In some implementations, the flow junction structure 120 may include only one type of inlet rather than main inlets and auxiliary inlets. In some implementations, the flow junction structure can incorporate flow/pressure sensors to measure and compare actual fluid flow. Such flow junction structures can provide additional data that can be used to confirm that the actual and intended flow rates are in agreement.

In some implementations, the system 100 includes an interface module 110 that serves as an interface between the computing device 115 and the multiple infusion pumps 105. The interface module 110 can feature a first set of ports to communicate with the computing device 115 and a second set of ports to communicate with the infusion pumps 105. The ports for communicating with the computing device 115 and the infusion pumps 105 can be substantially different. In such cases, the interface module 110 can serve as a bridge between the computing device 115 and the infusion pumps 105. For example, if an infusion pump 105a is configured to accept inputs only via a serial port whereas the computing device 115 features only a USB port as an output port, the interface module 110 can be used to provide communications between the infusion pump 105a and the computing device 115. In this case, the interface module 110 can include a USB input port to accept communications from the computing device 115 and a serial output port to communicate with the infusion pump 105a. In such a case, the interface module 110 also includes circuitry that is configured to forward communication received at the USB input port to the serial output port.

In some implementations, the multiple infusion pumps 105 in the system 100 can have different input ports. In such cases, the interface module 110 may feature various output ports configured to communicate with different infusion pumps 105. In general, the input and/or output ports of the interface module 110 can include, for example, a serial port, a parallel port, a USB port, an IEEE 1394 interface, an Ethernet port, a wireless transmitter, a wireless receiver, a Bluetooth module, a PS/2 port, a RS-232 port, or any other port configured to support connections off the interface module 110 with the computing device 115 and/or the infusion pumps 105. The interface module 110 can also include additional circuitry to facilitate communications between different types of input and output ports.

The interface module 110 can be implemented using any combination of software and/or hardware modules. Interface module 110 may be implemented as a stand-alone unit or could be incorporated within another device, e.g. the computing device 115 or the infusion pump 105. In some cases, the interface module 110 can include a processing device that allows implementation of additional functionalities on the interface module 110. For example, the interface module 110 can be configured to monitor the infusion pumps 105 (for example, in conjunction with various sensors) and provide the computing device 115 with appropriate feedback on the performance of the infusion pumps 105. In such cases, the processing device on the interface module 110 can determine whether or not certain feedback information is to be transmitted back to the computing device 115. In some implementations, the interface module 110 can also facilitate communications between the infusion pumps 105. In some implementations, the interface module 110 can also uniquely identify each infusion pump and corresponding data.

The computing device 115 can include, for example, a laptop, a desktop computer, or a wireless device such as a smart phone, a personal digital assistant (PDA), an iPhone, and a tablet device such as an iPad®. The computing device 115 can be configured to execute algorithms that determine the amount of fluids to be dispensed from the infusion pumps 105. In some implementations, the algorithms are implemented via software that can include a set of computer readable instructions tangibly embodied on a computer readable storage device. In some implementations, the computer readable storage device can be a non-transitory computer readable medium, for example, a hard disk, compact disk or a memory device. In some implementations, the computing device 115 can be configured to determine the amount of fluids to be dispensed from the infusion pumps 105 based in some implementations, on a mathematical model that characterizes fluid flow along the fluid path 123. For example, based on the mathematical model of fluid flow along the fluid path 123, the computing device 115 may determine amounts of fluid to be dispensed from the infusion pumps 105 such that a particular drug delivery profile is achieved at the delivery point 125. The computing device 115 communicates the determined amounts to the infusion pumps 105 either directly or via the interface module 110. The computing device 115 can be configured to communicate with the interface module 110 and/or the infusion pumps 105 via wired connections, a wireless network, or any combination thereof.

In some implementations, the system 100 includes at least one display. The display can be a part of one or more computing device 115, the interface module 110 or the infusion pumps 105. In other implementations, the display can also be a stand-alone unit coupled to one or more of the infusion pumps 105, or the interface module 110. The display can also be configured to present a console to the user that displays not only the numerical parameters, medication type, and details of the system, but also presents real time graphical representations of projected drug delivery profiles based on the parameters entered by a user. Based on these parameters, associated software can be configured to calculate and graphically display the intended drug delivery profile (the values selected by the user) as well as the projected drug delivery time course, for example, as determined by the model. When relevant, upper and lower safe boundaries for medication delivery rates can be superimposed on the graphs, and key inflection points and time intervals can also be indicated. The graphical displays can be updated in real time to reflect changes in parameters such as the carrier fluid flow rate and the drug flow rate. In some implementations, the display can include an E Ink screen, a liquid crystal display (LCD) or a light emitting diode (LED) screen. Wireless handheld devices such as an iPhone® or iPad® or the like can also be used as the display.

In some implementations, the computing device 115 can be configured to monitor flow profiles in various parts of the system 100. One or more sensors can be deployed in the various parts to detect such flow profiles. For example, a sensor may detect the actual amount of drug dispensed by the infusion pump 105a and provide the information to the computing device 115 via a feedback loop. Similarly, a sensor can also be deployed to detect the amount of carrier fluid dispensed by the infusion pump 105c. In some implementations, one or more sensors can detect various parameters of the mixed fluid in the fluid path 123. Such parameters can include, for example, a flow rate or velocity at a particular point, amount of a particular drug in the mixture, amount of carrier fluid in the mixture, etc. The data from the sensors can be analyzed at the computing device 115 (or possibly the interface module 110) and graphically represented on a display.

In some implementations, a visual and/or audible alarm can be triggered if certain parameters of the drug delivery profiles are detected to be out of a normal or safe range. For example, if an amount of drug predicted (e.g. by a predictive model) to be delivered at a future time is determined to be outside a permissible range, an audible and/or visual alarm can be triggered. In some implementations, an alarm can be triggered based on detecting when at least one of a current drug flow rate, a current carrier fluid rate or a predicted drug delivery profile is outside a corresponding pre-defined range. The corresponding pre-defined range can be pre-stored (e.g. in a drug-library or a database for storing drug related parameters) and made available to a computing device that determines whether an alarm should be triggered. The graphical displays can also be configured to visually reflect these alarms (for example, with flashing values or with color changes). The software can also be configured to trigger an alarm or warning based not only on unexpected or unsafe values at the current moment in time, but also based on such values that are predicted to occur in the future if current settings are maintained. Furthermore, the software can be configured to monitor for malfunctions via feedback from the pumps, such as the unplanned cessation of carrier flow, and provide warnings accordingly. Whether or not an alarm is to be triggered can be determined by the computing device 115, the interface module 110, or an infusion pump 105. Such alarms and drug libraries of acceptable drug parameters to which a particular drug profile is compared are described in further details in U.S. Pat. No. 5,681,285, the entire content of which is incorporated herein by reference.

The fluid path 123 facilitates propagation of fluids dispensed from the infusion pumps 105 (and mixed together at the flow junction structure 120) to the target 130. In general the fluid path 123 terminates at the delivery point 125. When the target 130 is a human patient or an animal, the delivery point 125 can facilitate, for example, intravenous, intraosseous, subcutaneous, arterial, intrathecal, or epidural delivery of fluid propagated through the fluid path 123.

The fluid path 123 can include one or more components. In some implementations, the flow junction structure 120 (e.g., a manifold) can be considered as a part of the fluid path 123. The fluid path 123 can also include, for example, one or more of a tube (e.g., an intravenous tube), a catheter (e.g., a vascular access catheter), a needle, a stopcock, and a joint. In some implementations, the components of the fluid path 123 can be represented using one or more corresponding structural parameters. Structural parameters can include, for example, number of inlets in a manifold, length, diameter or volume of a catheter, number of bends in the fluid path, and volume of the fluid path 123. In some implementations, the fluid path 123 can also include at least portions of a fluid path between an infusion pump 105 and the flow junction structure 120. In some implementations, the volume of the fluid path 123 is referred to as "dead volume." In some implementations the term "dead space" is used as an equivalent term for "dead volume".

Figure 1B:
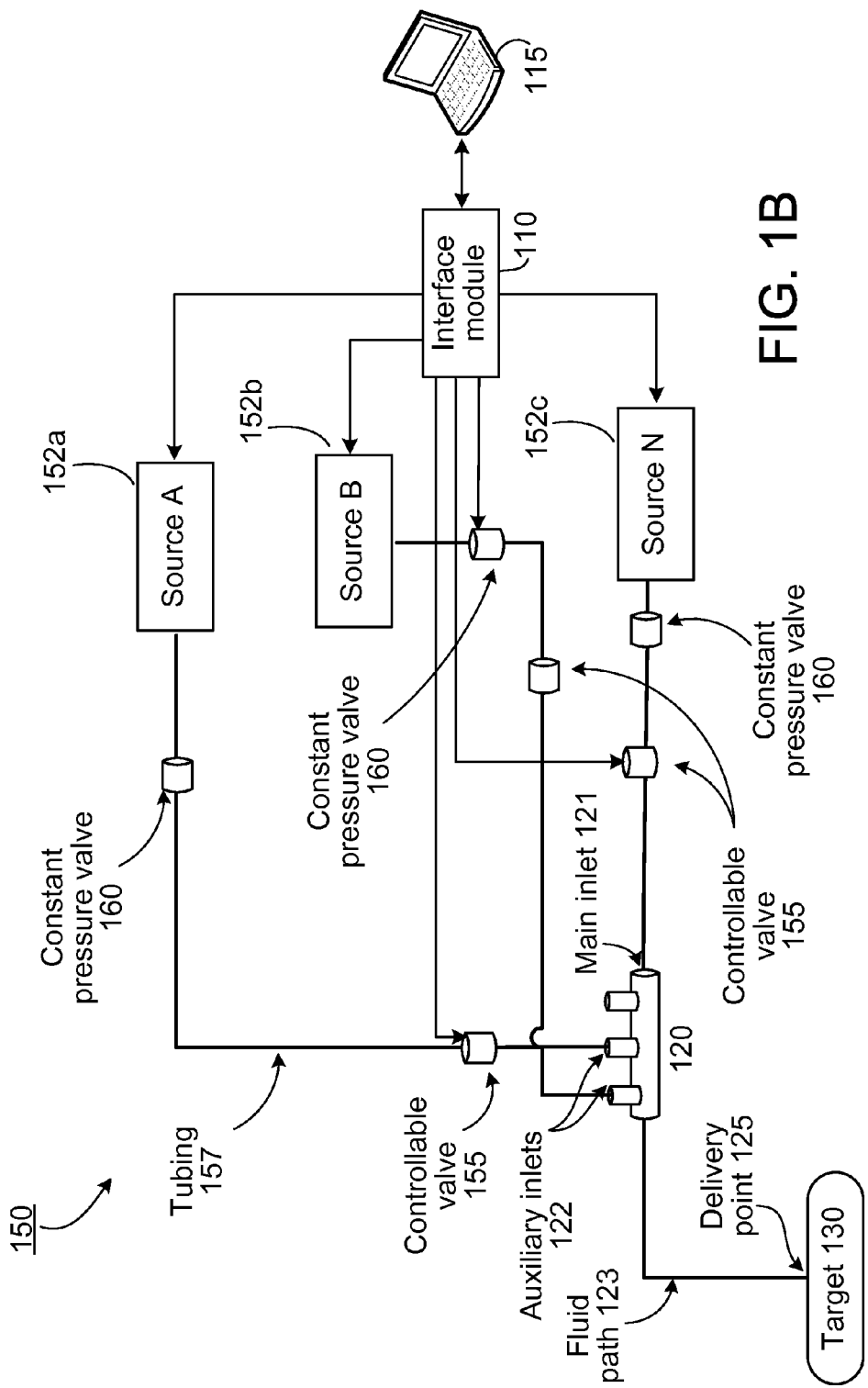
FIG. 1B is a schematic block diagram of another example of a system for controlling 2C fluid delivery.

FIG. 1B shows a schematic block diagram of another example of a system 150 for controlling fluid delivery. The system 150 includes multiple fluid sources 152a, 152b, and 152c (152, in general) that deliver fluids (e.g., drugs and carrier fluids) to a target 130. The fluids from the multiple sources 152 are mixed with each other at the flow junction structure 120 and transported along the fluid path 123 and delivered to the target 130 at the delivery point 125. One or more of the fluid sources 152 can be a container (such as an intra-venous (IV) fluid container) from which the fluid flows to the flow junction structure 120 due to gravity or additional methods of fluid delivery including, but not limited to, pressurization (internally or externally applied). One or more of the fluid sources 152 can be an infusion pump such as the infusion pump 105 described above with reference to FIG. 1A. In some implementations a combination of containers and infusion a pumps can be used as the plurality of fluid sources 152. For example, a drug can be provided from a container whereas the carrier fluid is provided from an infusion pump.

The system 150 further includes a controllable valve 155 between a source 152 and the flow junction structure 120. In some implementations, a controllable valve 155 can be placed between each source 152 and the flow junction structure 120. Alternatively, at least one of the sources 152 can be directly connected to the flow junction structure without an intervening controllable valve 155. In some implementations, when a controllable valve 155 is placed between a source 152 and the flow junction structure 120, the system 150 can also include a constant pressure valve 160 between the corresponding source 152 and the controllable valve 155. Thus, the constant pressure valve 160 is located "upstream" from the controllable valve 155.

The constant pressure valve can be configured to maintain a constant upstream pressure for a fluid that flows through the controllable valve 155. In some implementations, the constant upstream pressure can also be maintained by the source 152. For example, if the source 152 is a controlled infusion pump, the infusion pump can be configured to maintain the constant upstream pressure. In some cases, the constant pressure can also be maintained by gravity flow, intravenous pump flow, or other mechanisms. In some implementations, the intravenous pump can be used to provide a pressure difference in excess of a rated capacity of an in line constant pressure valve 160.

The controllable valve 155 can be configured to exert a controllable resistance to the flow that enters the flow junction structure 120. For example, the controllable valve 155 can be configured to restrict the flow in accordance with desired settings under constant upstream pressure. The desired settings can be deduced from fluid dynamics principles, for example, by applying the following equation:

$$Q = (K \cdot P \cdot r^4)/(n \cdot l) \quad (1)$$

where Q represents the flow,
K is a constant,
P represents the difference between upstream and downstream pressure,
r is the radius of the tube connecting the constant pressure valve and the controllable valve,
n represents viscosity of the fluid, and
l is the length of the tube.

Because the length of the tube is fixed, for a fluid of substantially constant viscosity, the flow is proportional to the fourth power of the radius. Therefore, the flow can be controlled if the radius (or cross sectional area) of the tube can be controlled using the controllable valve 155. Various types of controllable valves 155 can be used in methods and systems described herein. In some implementations, the controllable valve 155 is a pinch valve that can be configured to alter the cross-sectional area of a tube on which the valve is disposed. For example, the controllable valve 155 can include a jaw or clamp that can exert force on the tube to alter the cross-sectional area of the tube. In some implementations, a substantially continuous management of the internal diameter or cross-sectional area of the tubing 157 can provide for precise delivery of specified fluid volumes. Resistance to the flow, in some cases, can be proportional to an energy supplied to the valves 155. The supplied energy can be electrical, pneumatic, or of another form.

In some implementations, the controllable valve 155 can include one or more actuators that can be electrically controlled to vary the force exerted by the valve on the tube. The one or more actuators can include, for example, a shape memory alloy that changes shape based on a magnitude of an electric current passed through the alloy. The amount of force exerted by the controllable valve 155 can be controlled by varying, for example, the current through the shape memory alloy.

An example of a shape memory alloy is Ni—Ti, a nickel-titanium alloy. Other suitable shape memory alloy such as copper-zinc-aluminum-nickel, or copper-aluminum-nickel can also be used. Shape memory alloys typically undergo a thermo-elastic phase transformation from a martensitic phase when at a temperature below the material's phase change transition temperature to an austenitic phase when heated through the phase change transition temperature. Below the phase change transition temperature, the alloy is plastically deformed, and remains deformed until heated through the phase change transition temperature at which point it reverts to an original shape. The resistivity characteristic of the shape memory alloy material can be used for heating it to temperatures above the corresponding phase change temperature. For example, as current flows through an element made of a shape memory alloy, the element can be heated to a temperature above the phase transition temperature. This in turn can change the shape of the element. The shape memory alloy element can be disposed in the controllable valve 155 such that the element exerts a variable force on the jaw or clamp of the valve 155 in various states of deformity.

In some implementations, one or more of the controllable valves 155 can be controlled by electrical control signals from the interface module 110. The control signals can be based on a desired amount of flow through the corresponding controllable valve 155 and can be determined using the predictive models described herein. In some implementations, the flow rates from the sources are not controlled by the interface module, instead, the flow is controlled by controlling the controllable valves 155 under a constant pressure, which can be ensured by the constant pressure valve 160. In some implementations, the interface module 110 can be used to control one or more sources 152 and one or more controllable valves 155. For example, a drug flow can be controlled via a controllable valve 155, while the carrier fluid is controlled by controlling the output of the source. In some implementations, the control signal from the interface module can be converted to a different form (e.g., a mechanical or pneumatic force) to drive the actuator.

The tubing 157 on which a controllable valve is disposed is typically made of a flexible material (e.g., silicone) such that a force exerted on the tubing 157 can alter the cross-section of the tubing thereby impacting an amount of fluid that can flow through the cross-sectional area. However, other materials or structures that allow alteration of flow rates through the tube by a controllable valve 155 are within the scope of this disclosure.

Figure 1C:
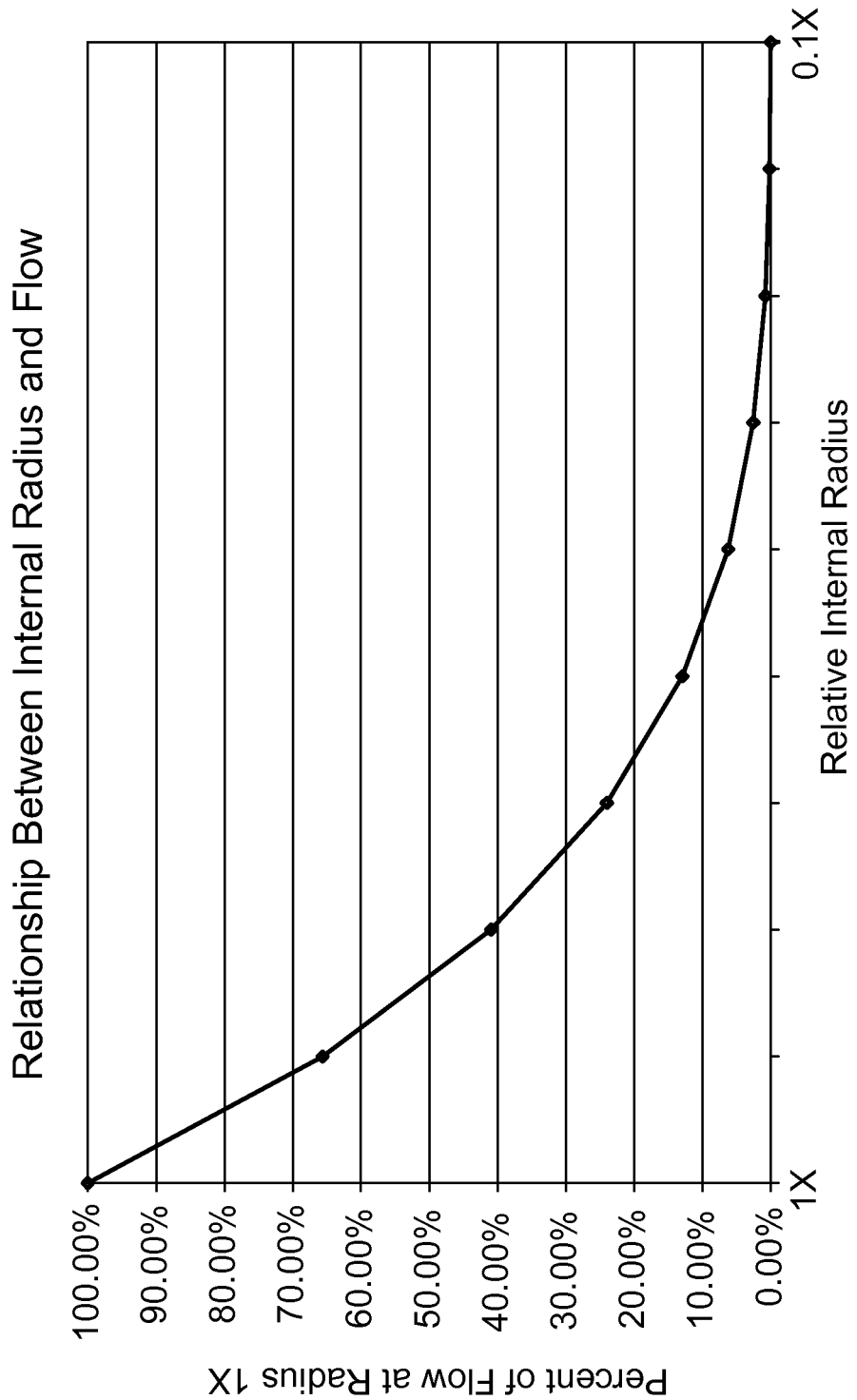
FIG. 1C is a plot showing a relationship between an internal radius of a tube and a flow through the tube.

Using equation (1), a relationship between the flow Q and the internal radius r (and consequently the cross-sectional area) can be calculated for any given change in the pressure P, tubing length l and fluid viscosities n. FIG. 1C shows a relationship between an internal radius of a tube and the flow Q assuming a constant pressure drop, constant tubing length, and constant fluid viscosity. The example in FIG. 1C shows that the flow rate reduces at a non-linear rate as the radius of the tube is reduced to about 10% (0.1×) of the original radius (1×). Because the amount of power consumed to control the controllable valves is typically less than the amount of power consumed to control the sources 152, the controllable valve approach can be used for low power applications such as portable and/or battery operated drug delivery systems. Other settings in which the system 150 can be used include, for example, critical care units, including those specializing in the care of critically ill pediatric patients, operating rooms for the delivery of intravenous anesthesia, and interventional procedure rooms including cardiac catheterization rooms.

Figure 2:
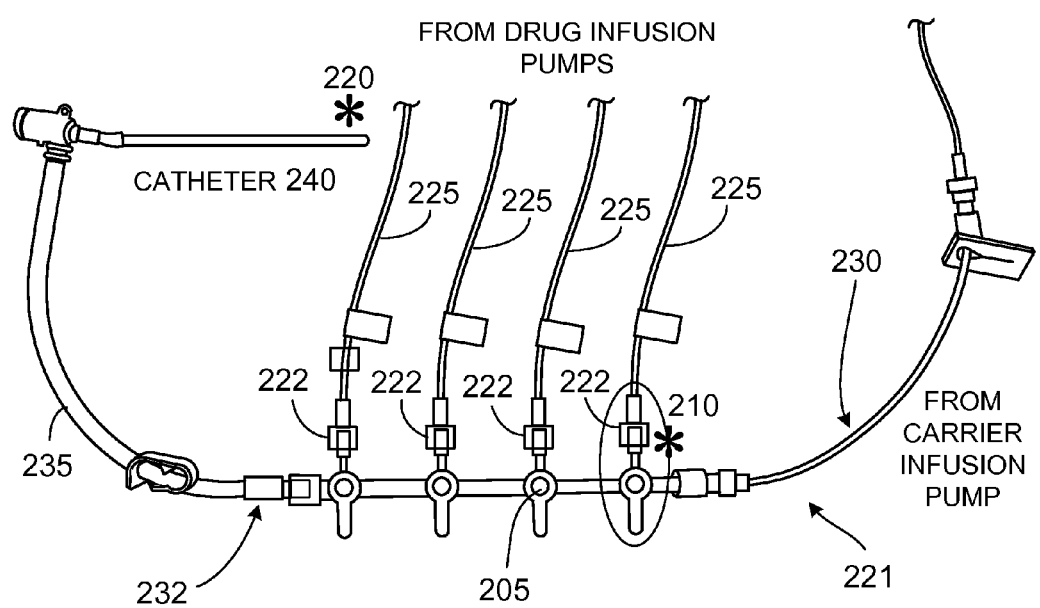
FIG. 2 is a diagram of an example of a flow junction structure.

Referring now to FIG. 2, an example of the dead volume is illustrated via a manifold 205, an example of a flow junction structure. The manifold 205 includes four auxiliary inlets 222 and one main inlet 221. The auxiliary inlets 222 facilitate connections with tubes 225 originating from drug infusion pumps. The main inlet 221 facilitates a connection with a tube 230 originating from a carrier infusion pump. In some implementations, the drug infusion pumps and the carrier infusion pump can be substantially similar to the infusion pumps 105 described with reference to FIG. 1A. A tube 235 is connected to the outlet 232 of the manifold 205. The tube 235 connects the manifold 205 to a catheter 240. In some implementations, the catheter 240 can include an introducer or sheath of various sizes, such as a 9 Fr Introducer, an 8 Fr sheath, or an 8.5 Fr. sheath. In some implementations, the catheter can include any standard single or multiport central venous catheter (including catheters sized for adults or catheters sized for pediatric patients), and pulmonary artery catheters. In some implementations, the catheter can be a peripheral venous catheter, or an intra-arterial, intra-osseous, intrathecal, epidural, subcutaneous or other catheter or cannula device. In this example, the dead volume is the volume between the asterisk 210 and the asterisk 220. The asterisk 210 represents the point where a drug first joins the carrier fluid and the asterisk 220 denotes the point where a mixture of the drugs and the carrier fluid enters a target (e.g. patient's bloodstream). In this example, the asterisk 220 also represents the delivery point 125 described with reference to FIG. 1A.

In general, the dead volume constitutes a space that must be traversed by the mixture of drugs and carrier fluid before reaching the target 130. In some implementation, the carrier fluid can be used to speed propagation across the dead volume. However, in some cases, including those implementations where drug and/or carrier flows are low, the dead volume can cause a considerable delay for a drug dispensed by an infusion pump in reaching the target 130. In some implementations, the dead volume acts as a reservoir for a drug that is inadvertently delivered when flows are altered. In some implementations, discordance between the intended delivery profile (based on drugs dispensed at a corresponding infusion pump 105) and the actual delivery profile at the delivery point 125 can be avoided by algorithmically controlling the flow in the fluid path 123, based, for example, on a predictive model of the flow. Such algorithms can take into account factors including, for example, the dead volume, parameters of the flow junction structure 120 (e.g. a manifold), components of the fluid path 123 (e.g. an intravenous tube, and an intravascular catheter, etc.), alterations in flow rates of the drugs and the carrier fluid, and relationships between such flow rates. In some implementations, appropriate algorithmic control of the flow in the fluid path reduces (or at least renders deterministic) a delay in delivering an intended dose of drug to the target 130 at a desired time.

Modeling the Mixed Flow

Modeling the mixed flow (i.e., mixture of the one or more drugs and the carrier fluid) can allow for algorithmically controlling the time course of the delivery (delivery profile) of the drugs thereby rendering the use of drug infusion systems safer and more predictable. In some implementations, the model of the mixed flow can be used to provide guidance, monitoring, visualization and control of drug infusion.

In some implementations, visualizations based on the model can enhance the safety of drug infusions by providing graphical displays of future drug delivery profiles. For example, graphical representations based on the model can show clinicians the predicted results of their decisions about drug dosing, carrier flow rates, and selection of vascular access catheters and manifolds. In some implementations, the model can also be used for training purposes. For example, the model can be used as the basis of an educational software package or simulator for training clinicians (nurses, physicians, pharmacists) in the real-life behavior of drug infusion systems.

In some implementations, modeling the mixed flow includes characterizing the flow using differential equations derived from physical principles. Because various parameters are considered and accounted for in the model, the model is also referred to as a unified model. The unified model takes into account multiple factors, including, for example radial diffusion (molecules moving toward the walls of a tubing or catheter), axial diffusion (molecules moving along the axis of flow), laminar flow (smooth bulk fluid flow), and physical chemical properties of the drugs, and the interactions between these and other factors.

In some implementations, only the drug flow (or the drug concentration along the fluid path over time) can be modeled to control the delivery profile of the drug. Various predictive models can be used for modeling the drug flow, drug concentration and/or the mixed fluid flow. An example of a model is described next in connection with modeling the mixed flow. The described model can be readily extended for modeling other flows such as the drug flow or the carrier fluid flow. It should also be noted that the following model is described for illustrative purposes and should not be considered limiting. Other predictive models that characterize the drug concentration along the fluid path over time, drug flow, carrier flow, or mixed flow are within the scope of the disclosure.

In some implementations, the mixed flow is modeled using a Taylor dispersion equation that includes parameters for radial diffusion, axial diffusion, and laminar flow. Taylor dispersion typically deals with longitudinal dispersion in flow tubes, but can also be expanded for any kind of flow where there are velocity gradients. In some implementations, the Taylor dispersion used for modeling the mixed flow can be represented as:

$$\frac{\partial \bar{c}}{\partial t} + \bar{u}\frac{\partial \bar{c}}{\partial x} = \left(\frac{R^2 \bar{u}^2}{48D} + D\right)\frac{\partial^2 \bar{c}}{\partial x^2} \qquad (2)$$

where D represents a molecular diffusion coefficient, u represents an axial velocity of fluid through a tube, x represents an axial distance along the tube, t represents time, R represents a radius of the tube, and c represents a concentration of a substance (e.g., a dye or a drug). The small bar over the parameters u and c represents a mean or average value. The average of the concentration of the substance is calculated over a cross-section of the tube. The flow is generally assumed to be non-turbulent and can be represented using a low Reynolds number. Reynolds number is a dimensionless number that gives a measure of the ratio of inertial forces to viscous forces and quantifies the relative importance of these two types of forces for given flow conditions.

In some implementations, equation (2) can be implemented numerically using forward difference models. Under an experimental setup, the model represented by equation (2) can be verified by tracking a dye as it flows through a fluid pathway via quantitative spectrophotometry measurements. The parameters in the model can be determined in various ways. For example, the molecular diffusion coefficient D (the unit of which can be $cm^2$/sec) can be retrieved or calculated based on known measurements, or can be estimated experimentally based on the properties of the drug molecules. In such cases, the value of D can vary from one drug to another. In some implementations, the mean axial velocity of the fluid can be calculated from the total flow rate and properties of the fluid path 123. In some implementations, the equations related to the model are solved for the concentration of the substance (drugs, carrier fluid etc.) averaged over the cross section of the fluid path 123. The equations can be solved over the length of the fluid path for a given time.

In some implementations, the model uses an empirical dead volume of the fluid path 123 rather than a measured dead volume. The empirical dead volume accounts for irregularities in the fluid path 123 including, for example, changes in diameter between stopcocks, manifolds, tubes, etc., and changes in angles (e.g., stopcock ports can meet manifolds at right angles) in the fluid path 123. The empirical dead volume can be determined experimentally, for example, by examining a series of candidate empirical dead volumes and selecting one that best fits an experimental control curve in a least squares sense. In some implementations, other model parameters may also be determined experimentally. The use of empirically-determined parameters can avoid the need for complicated, computationally-intensive modeling based on precise physical characteristics of infusion setups that may vary between clinical situations. Similarly, other parameters (e.g. parameters related to fluid propagation properties through the fluid path 123) can also be empirically estimated or calibrated using an appropriate control curve.

In some implementations, parameters, including empirical dead volumes, can be stored in an electronic library that includes information on infusion sets and their individual components such as drug pumps, manifolds, tubing, catheters (including individual lumens of multi-lumen catheters), connectors, stopcocks, etc. This infusion system component library can be used in conjunction with the system described in this document. Physical parameters that can be stored in such a library include the dead volume of each individual element, and structural information such as inner diameter, length, and architecture of the fluid path. Such architecture information can include a number of right angle bends in the fluid path (or other flow angle changes) and changes in the diameter of the fluid path. The stored information can be specific for each physical element that is used within a fluid delivery pathway. The electronic library can be integrated with the system described in this document for use in any of the visualization, prediction, and control modes. In some implementations, the details of each fluid pathway physical element available to a clinician within an institution are loaded within an institution specific component library.

In some implementations, the catheters and other infusion system elements can be identified via barcode, RFID, or similar tagging technology to facilitate easy, automated or semi-automated identification of the catheters or the other infusion system elements. Alternatively, or in conjunction with such identification methods, the elements can be selected from the infusion system component library via, for example, scrollable or pull-down menus provided as a part of a user interface.

In some implementations, solving the unified model equations yields the concentration of drug along the fluid path 123 from the point where a drug joins the carrier stream (e.g., the point 210 in FIG. 2) to the distal tip of an intravascular catheter (e.g., the point 220 in FIG. 2) at any given time and predicts how the concentration will evolve along the fluid path 123. Knowledge of the drug concentration at various portions of the fluid path 123 can be useful in predicting a time course of drug delivery to the target 130. Knowledge of such a time course can be used to create control algorithms that achieve precise control of drug dosing. In some implementations, the equations can be solved using approximation methods such as a forward difference numerical approximation. The forward difference numerical approximation can include dividing the fluid path 123 (that, in some implementations, can include a manifold, an intravenous tube and a catheter) into many small discrete segments. In such cases, a solution for the concentration of drug in each segment can be calculated for each incremental time step, thereby yielding an accurate estimate of the drug delivery (for example, at the delivery point 125) over time. In some implementations, other numerical approximation algorithms, including other finite difference methods such as backward difference or central difference numerical approximations, can also be used to solve the equations.

In some implementations, rapid control of ongoing changes in drug delivery is based on physical principles that include one or more of a relationship of flow rate and drug concentration to drug delivery, a relationship of the drug concentration in the mixed fluid to the ratio of drug flow to carrier flow, rapid transmission of flow alterations based on the incompressibility of the fluid and limited compliance of the elements of the infusion system fluid path. In some cases, drug delivery (mass/time) can be considered as substantially equal to flow rate (volume/time) times drug concentration (mass/volume). The drug concentration in the mixed fluid is substantially equal to the ratio of drug fluid flow divided by total (mixed) fluid flow (the ratio being a dimensionless number) multiplied by the original drug concentration in the (unmixed) drug flow. In some implementations, alterations of the drug flow and carrier flow can be made in parallel, keeping the ratio of drug flow to mixed fluid flow at a constant value. In some implementations, this type of control facilitates maintaining a constant drug concentration in the mixed fluid and making precise changes in drug delivery as described further in the next section. In some implementations, maintaining constant mixed drug concentrations can be done in conjunction with algorithms based on predictive models or other algorithms that do not directly depend on predictive models.

In some implementations, algorithms based on maintaining a constant mixed drug concentration (as described above) can be used in conjunction with algorithms built on predictive models to minimize total fluid delivery while enabling rapid and precise changes in drug delivery.

Applications

The methods and systems described herein can be used in various ways to achieve useful results. For example, predictive models such as the model described above and other principles described above, including maintenance of constant mixed drug concentration, can be applied at various stages of a drug delivery process in a drug delivery system (e.g., the system 100 described with reference to FIG. 1A). Some such applications are described below as examples.

Reduction of Drug Delivery Onset Delay

In some cases, drug delivery onset delays can be reduced by controlling drug infusion pumps using algorithms based on a model of the flow in the fluid path. Such an onset delay can be manifested in a lag between an activation of a drug infusion pump and the time when the appropriate amount of drug actually reaches the target such as the patient's bloodstream. Such lags can have high clinical significance and consequences, particularly in critical care settings where rapid drug administration could be important and carrier and drug infusion flow rates are typically low. Reducing the lag by simply increasing the carrier fluid flow rate can have undesirable results. For example, a high level of carrier fluid flow (if maintained) can sometimes lead to excessive volume delivery to patients. Decreasing the carrier fluid flow, on the other hand, can also decrease drug delivery.

In some implementations, the carrier fluid and drug flow proportions can be maintained in lock-step (i.e., at a constant ratio) to achieve a fixed concentration of drug along the fluid path 123. A coordinated control of the carrier fluid infusion pump in conjunction with the drug infusion pumps (e.g., the infusion pumps 105a and 105b in FIG. 1A) can provide rapid and responsive control by maintaining proportionality between the drugs and the carrier fluid in the fluid path 123.

In some implementations, reduction of drug delivery onset delay can be achieved by initially setting high carrier and drug flows and maintaining those flows for a given period of time, e.g., one time constant (with the time constant defined as the dead volume, or empirical dead volume, divided by the total flow rate), then turning the carrier and drug flows immediately down to steady state levels. In some implementations, this involves initially setting carrier flow to the maximum allowable rate and setting the drug fluid flow at a rate that achieves a drug concentration in the fluid path equal to what the drug concentration will be when the carrier and drug flow are reduced to steady state levels. Carrier and drug flows are initially kept at high levels for one time constant and then reduced to target levels. As described in the previous section, maintaining proportionality between carrier and drug flows keeps drug concentration constant. In such implementations, there may be a brief undershoot of drug delivery as flows are turned down, but target drug delivery rates are achieved relatively quickly. This also provides a means to limit fluid volume delivery to the patient.

Figure 3A:
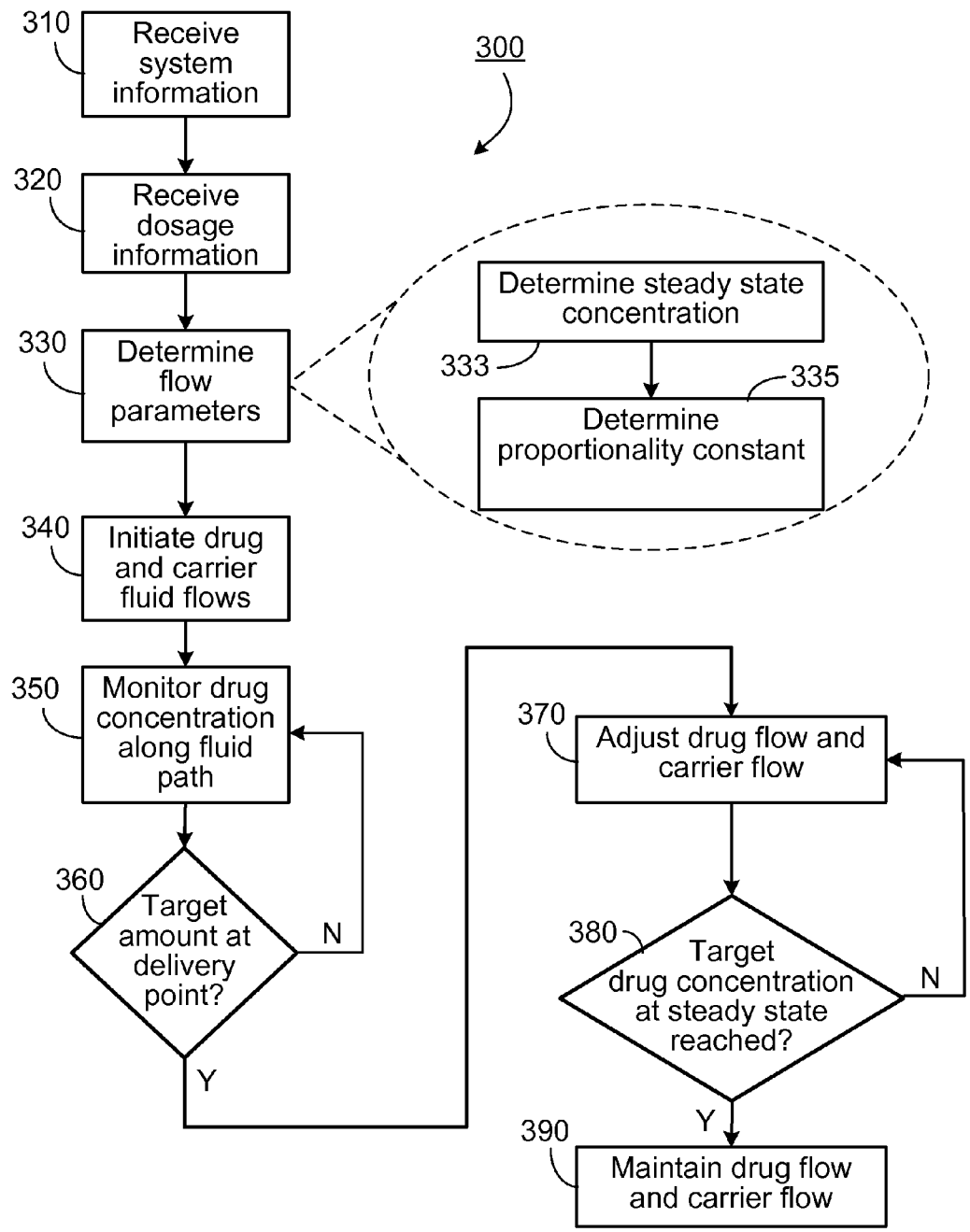
FIG. 3A is a flowchart of an example of a sequence of operations for reducing drug delivery onset delay.

FIG. 3A shows a flowchart 300 depicting an example of a sequence of operations for reducing drug delivery onset delay. The sequence of operations shown in the flowchart 300 can be executed, for example, in a system substantially similar to the system 100 described with reference to FIG. 1A.

Operations can include receiving (310) system information at a processing device. The system information can include information and parameters related to a drug infusion system substantially similar to the system 100 described with reference to FIG. 1A. In some implementations, the system information includes parameters related to one or more of a flow junction structure (e.g., a manifold), a drug infusion pump, an intravascular catheter, an intravenous tubing etc. For example, the system information can include information on the diameter of cross section of an intravenous tube, maximum output rate of an infusion pump, a length of an intravenous catheter, number of inlets of a manifold, position of stopcocks in a tube, and the material of a tube. The system information can be used for determining the parameters in equations used in modeling the flow in a fluid path.

In some implementations, the system information is manually input by a user (e.g., a clinician) via an input device coupled to a computing device (e.g. the computing device 115). In some implementations, the computing device can be configured to access a database that stores the system information (e.g., organized, for example, as libraries) for various systems. For example, relevant information for an infusion pump 105 can be stored in the database as a library linked to the particular type of infusion pump. Similarly, information on other components of the system, such as manifolds, tubes, catheters, etc., can also be stored in the database. The database can, in some implementations, store information about physical or chemical properties of individual infused drugs. The database can also be configured to store, for example, a visual and/or numerical history of pump input parameters and calculated drug delivery profiles.

The computing device can be configured to access the database to retrieve information on a component device upon detecting and/or identifying the presence of the component device in the system. In some implementations, the computing device identifies the component device based on a manual user input. In some implementations, the computing device can also be configured to automatically identify the component device automatically, for example upon reading an identification tag (e.g., a radio frequency identification (RFID) tag, or a barcode) of the component device. In such cases, the computing device may communicate with a tag reader (e.g., a RFID reader or a barcode scanner) to identify the component device. The tag reader can identify a component device and provide the computing device with related parameters (e.g. structural parameters) associated with the component device. In some cases, the parameters associated with the component device can be retrieved from a database. In some such identification may also be facilitated by near field communication (NFC) technology.

Operations also include receiving (320) dosage information at a computing device. The dosage information can be received at the computing device manually from a user (e.g., a clinician) or retrieved automatically from a database. The dosage information can include various parameters, for example, a target amount of drug to be delivered to the target, a time of drug delivery, a carrier flow rate $Q_c$, a drug flow rate $Q_d$, a total flow rate $Q_T$, a drug delivery rate dd, a target drug delivery rate $dd_{target}$, a steady state rate ss, maximum allowable carrier flow $Q_{cmax}$, a target steady state carrier flow $Q_{css}$, a stock drug concentration $c_d$, etc. Some of these parameters can be calculated from the other parameters; for example, the total flow rate can be calculated as the sum of the drug flow rate $Q_d$ and the carrier fluid flow rate $Q_c$. In some implementations, the dosage information can also include information on safe ranges associated with a given drug. Such information can be used for triggering alarms for overdose.

Operations can also include determining (330) flow parameters. The flow parameters can include, for example, drug flow rate at steady state $Q_{dss}$, total flow rate at steady state $Q_{Tss}$, mixed flow concentration at steady state $c_{ss}$, a proportionality constant between the steady state carrier flow rate and the steady state drug flow rate, etc. In some implementations, the initial flow parameters are determined as a combination of received and calculated values. For example, the initial carrier flow level can be set at the maximum level $Q_{cmax}$ and the initial drug flow can be set at a rate that achieves a mixed drug concentration (in the most proximal, upstream, portion of the mixed fluid) equal to the desired steady state drug concentration.

In some implementations, determining the flow parameters can include determining the steady state concentration c, of the mixed flow (i.e., mixture of drug and carrier fluid) (333). The steady state concentration of the mixed flow can be calculated, for example, from values of $Q_{dss}$ and $Q_{cTss}$. Such calculations can be represented using the following equations:

$$Q_{dss} = dd_{target}/c_d \qquad (3)$$

$$Q_{Tss} = Q_{css} + Q_{dss} \qquad (4)$$

$$c_{ss} = (Q_{dss}/Q_{Tss})^* c_d \qquad (5)$$

Determining the flow parameters can also include determining the proportionality constant p (335). In some implementations, the proportionality constant represents the ratio between the steady state carrier flow and the steady state drug flow and is given by:

$$p = Q_{css}/Q_{dss} \qquad (6)$$

Operations can also include initiating drug and carrier fluid flows (340), in accordance with the determined flow parameters, and the received system and dosage information. In some implementations, the carrier fluid flow is initiated at the maximum allowable rate such that:

$$Q_c = Q_{cmax} \qquad (7)$$

In some implementations, the drug flow can be initiated such that the proportionality constant is maintained for the maximum allowable carrier flow. In such cases, the drug flow is given by:

$$Q_d = Q_{cmax}/p \qquad (8)$$

Operations further include monitoring drug concentration (350) along the fluid path over time using, for example, the forward difference model based on the Taylor dispersion equation (equation 2). This can include solving for the drug concentration as a function of the axial distance x along the fluid path and time t. The drug concentration can therefore be represented as c(x, t). In some implementations, the drug delivery rate dd at the delivery point is monitored. Representing the effective length of the tube or fluid path as L, the amount of drug delivered can be represented as:

$$dd = c(L,t)^* Q_T \qquad (9)$$

Operations further include periodically checking (360) if the drug delivery rate at the delivery point substantially matches the target drug delivery rate $dd_{target}$. In some implementations, the time intervals can be represented as dt. If the drug delivery rate does not match the target delivery rate, the monitoring is repeated after another time interval dt.

If the drug delivery rate dd at the delivery point substantially matches the target drug delivery rate $dd_{target}$, operations can include adjusting (370) the drug flow and the carrier flow. In some implementations, one or more of $Q_c$ and $Q_d$ are reduced in a controlled fashion. For example, just after dd reaches the target drug delivery rate ddtarget, $Q_c$ and/or $Q_d$ can still be at the high initial values. In such cases, $Q_c$ and $Q_d$ may have to be reduced while maintaining the target drug delivery rate $dd_{target}$ as well as the proportion of drug flow and carrier fluid flow represented by p. In some implementations, $Q_c$ and $Q_d$ are adjusted by controlling the respective infusion pumps.

In some implementations, $Q_c$ and/or $Q_d$ are adjusted based on predicting a concentration of drug that will arrive at the delivery point after a particular time. This can be done using the model of flow in the fluid path. For example, a current velocity of the mixed fluid (derived, for example, from $Q_T$ and possibly the architecture of the fluid path) can be used to find a position $x_1$ that would arrive at the delivery point after a time dt if the current $Q_T$ is maintained. This position can be determined, for example, as:

$$x_1 = L - u(t_{current}) dt \qquad (10)$$

where L is the length of the fluid path used in the model and $u(t_{current})$ is the current velocity of the mixed fluid. In the above case, the concentration of drug expected after time dt is therefore given by $c(x_1, t_{current})$ calculated using the model. In some implementations, the calculated drug concentration can be used to calculate new flow rates that would maintain the target drug delivery rate $dd_{target}$ at the delivery point. For example, the new flow rates can be calculated as:

$$Q_{Tnew} = dd_{target}/c(X_1, t_{current}) \qquad (11)$$

$$Q_{dnew} = Q_{Tnew}/(1+p) \qquad (12)$$

$$Q_{cnew} = Q_{Tnew} - Q_{dnew} \qquad (13)$$

where $Q_{Tnew}$, $Q_{dnew}$, and $Q_{cnew}$, represent the new total flow rate, the new drug flow rate, and the new carrier fluid flow rate, respectively. The existing carrier fluid flow rate and the existing drug flow rate can then be replaced by the new calculated flow rates as:

$$Q_c = Q_{cnew} \qquad (14)$$

$$Q_d = Q_{dnew} \qquad (15)$$

Operations can also include checking (380) if the drug concentration at the delivery point substantially matches the steady state concentration $c_{ss}$. This can be represented as:

$$c(L,t) = c_{ss}? \qquad (16)$$

In some implementations, the check can be performed periodically after time intervals dt. If the steady state concentration is not reached, operations can include adjusting (370) the drug and carrier fluids flow again. If the steady state concentration is reached, operations can include maintaining (390) the drug and carrier fluid flows at the last calculated levels. In such cases, the following conditions are fulfilled:

$$dd = dd_{target} \qquad (17)$$

$$c(x,t) = c_{ss} \qquad (18)$$

for all x along the fluid path.

Figure 3B:
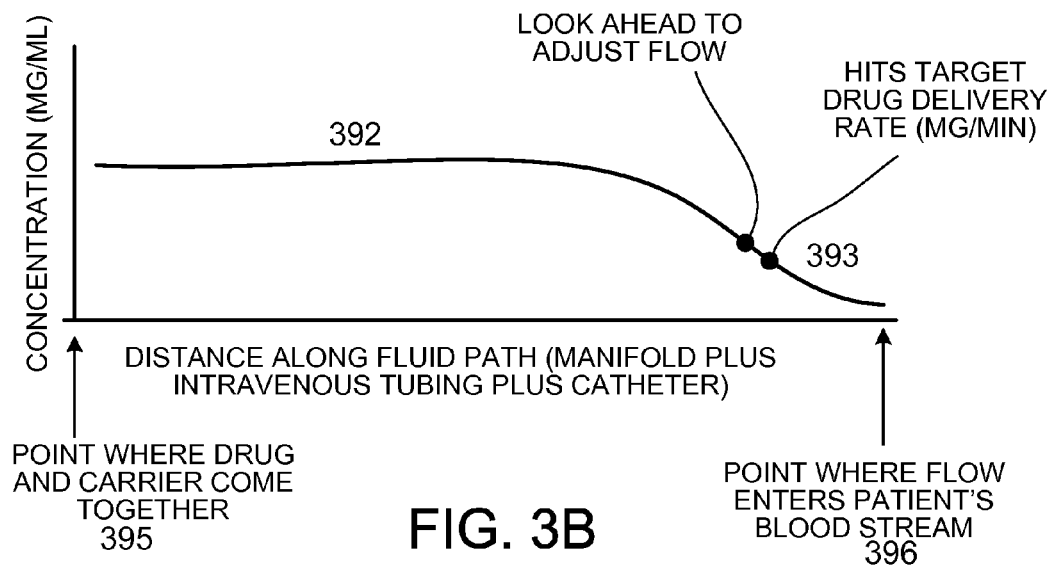
FIG. 3B is a schematic graph of an example of a concentration of a drug along a fluid path.

In an example use case of the sequence of operations described above, a clinician can initially choose a target carrier flow and a maximum allowable carrier flow, as well as the target drug delivery rate. The choice of the clinician is then received at the computing device controlling the infusion pumps. Characteristics of the infusion system (manifold, intravascular catheter, and any intravenous tubing that may be used) are also entered, detected or received, such that the dead volume or the empirical dead volume can be considered in the computations. Initially the carrier flow is kept at the maximum possible level and the drug flow is set at a level that achieves a drug concentration along the upstream portion of the fluid path identical to what the final drug concentration will be when carrier and drug flows are reduced to steady state levels. As the infusion pumps start, the drug is quickly swept down the fluid path toward the patient, traversing the dead volume of the infusion system. As the drug moves along the fluid path, the model is used to track the progress. FIG. 3B shows an example schematic graph of the concentration of drug along the fluid path (referred to in the figure as 'distance along fluid path') at a given moment in time. The point 395 represents the location where the drug and the carrier fluid come together, and the point 396 represents the location where the mixed flow enters the patient's bloodstream. The curve 392 shows diffusion of the leading edge of the drug, which is why it has the appearance of a wave rather than a step function.

Continuing with the example, the model keeps track of the drug flow and concentration (drug delivery) reaching the patient (i.e. reaching the point where the vascular access catheter terminates in the blood stream). The drug delivery rate (mass/time) can be represented as the fluid flow rate (volume/time) times the concentration of drug (mass/volume). Referring again to FIG. 3B, as the leading edge of the wavefront reaches the patient, drug delivery rises until at some point 393, the target drug delivery is reached. At this point, the model calculations can be used in a form of "intelligent feedback" or "adaptive" control to anticipate the drug concentration that would reach the patient one tiny increment of time later if flow were to remain unchanged. Based on this knowledge of the potential upcoming drug delivery, the carrier and drug flows can be adjusted to maintain drug delivery at the target rate. The proportionality between carrier and drug flow is maintained such that drug concentration along the rest of the fluid path remains at the same fixed level. At each time increment, the drug and carrier flows are adjusted downward, always maintaining fixed drug concentration along the rest of the fluid path, until the plateau drug concentration hits the patient's bloodstream. At that point, carrier and drug flow are both at the desired steady-state rates; and drug delivery is also at the steady-state target.

Although the changes to carrier and drug flow are made at the infusion pumps, these changes in flow are approximately instantaneously transmitted to the "patient end" of the fluid path due to the incompressible nature of the fluid.

In some implementations, algorithms as described for controlling rapid onset of drug delivery also provide a means to limit fluid volume delivery to the patient; this may be most important for patients who, due to organ system dysfunction, may not tolerate excess volume. Compared to conventional means of initiating drug onset (introducing a drug at the desired flow rate while leaving carrier fluid flow unchanged), rapid onset algorithms, such as described here, deliver minimal additional total fluid.

Figure 3C:
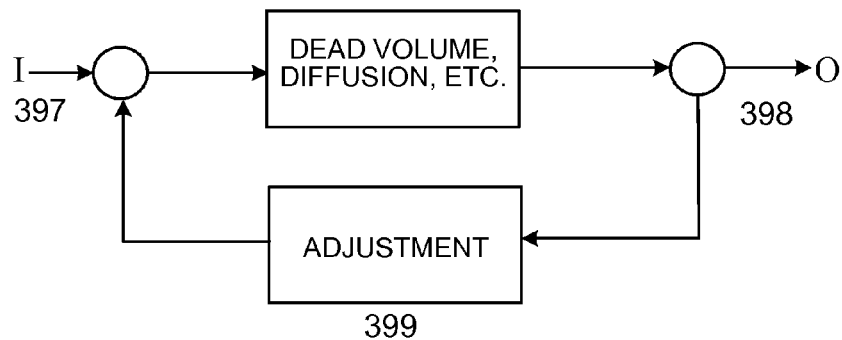
FIG. 3C is a block diagram of a feedback loop.

An example of an algorithm feedback loop is shown schematically in FIG. 3C. In this illustration, the input (I) 397 is the drug and carrier flows, for example, as set at the infusion pumps. Between the pumps and the patient, factors such as diffusion and dead volume can affect the time course of the drug reaching the patient (O) 398. Feedback gleaned using the model described above can be used to make appropriate adjustments 399 to the input 397 as indicated by a feedback loop in FIG. 3C.

Controlling Changes in Drug Delivery Profiles

In some cases, the infusion pumps can be adjusted to change a drug delivery profile (for example to change a dose) to be delivered to the target. In some cases, the disparity between the timing of changes to the pump settings and the actual time that the target drug dose reaches the target (e.g. a patient's bloodstream) can be significant. The methods and systems described herein can also be used for achieving precise control of changes in drug delivery profiles.

In some implementations, ongoing changes in drug delivery profiles (e.g., increases or decreases) can be achieved almost instantaneously via adjustments in the total flow (drug plus carrier). Such adjustments can be based on maintaining proportionality between carrier and drug flows, and hence a fixed concentration of drug along the fluid path. For example, to double drug delivery, total flow can be increased two-fold by doubling each of the carrier and drug flows. Typically, the incompressibility of the fluid allows such changes in the flow to be reflected immediately at the target end of the fluid path. In some implementations, because the drug concentration is kept constant along the fluid path, changes in target drug delivery profiles (mass/time) can be reduced to changes in the total flow (volume/time), with the model being used in calculating appropriate drug and carrier flows.

Figure 4:
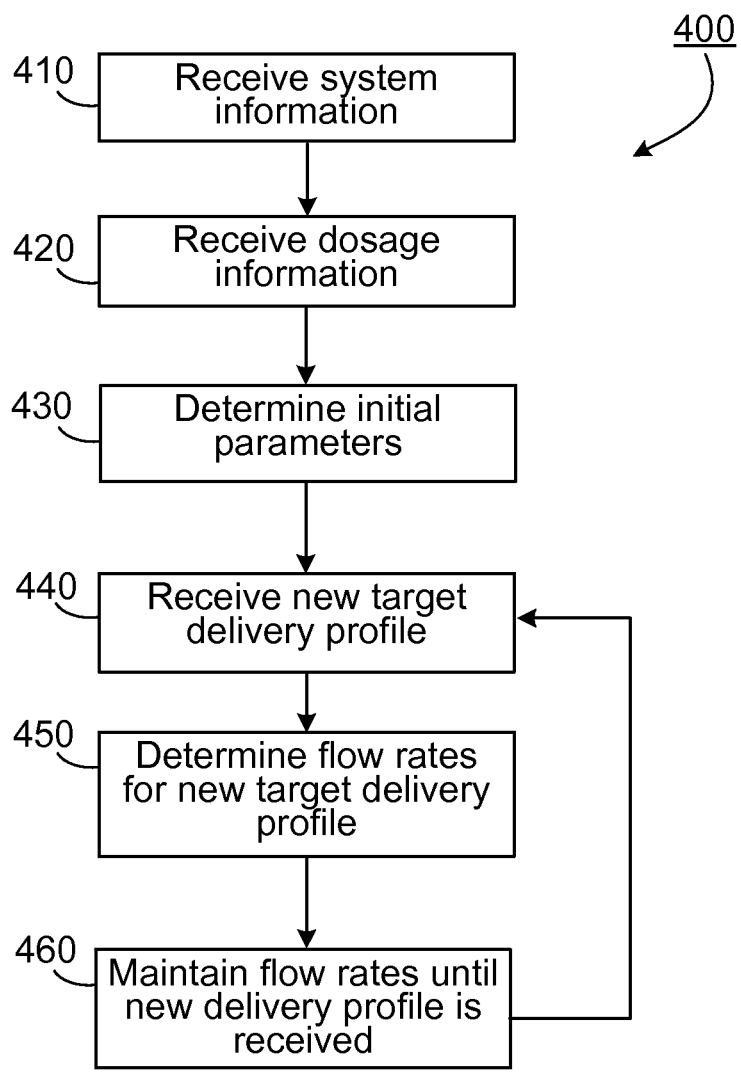
FIG. 4 is a flowchart of an example of a sequence of operations for controlling drug delivery profiles.

FIG. 4 shows a flowchart 400 depicting an example sequence of operations for controlling drug delivery profiles. The sequence of operations shown in the flowchart 400 can be executed, for example, in a system substantially similar to the system 100 described with reference to FIG. 1A.

Operations can include receiving (410) system information at a processing device. The system information received can be substantially similar to the system information described above with reference to operation 310 in FIG. 3A. The system information may be received via manual or automatic inputs. For example, the system information can be manually input by a user (e.g. a clinician) via an input device coupled to a computing device (e.g. the computing device 115). Alternatively, the system information may also be retrieved (e.g. from a database) or automatically identified (e.g. by reading an RFID tag, or a barcode) of a component device.

Operations also include receiving (420) dosage information. In some implementations, the dosage information can include an initial carrier fluid flow and drug flow (represented as $Q_{c0}$ and $Q_{d0}$, respectively). In some cases, the initial flows can be the flows at the steady state. The dosage information can be received from a user (e.g. a clinician) or retrieved automatically. For example, the initial flow values can be received from the infusion pumps, or from one or sensors monitoring the flow rates dispensed by the pumps. The dosage information can also include desired changes in target drug delivery profiles $dd_{target}$ at one or more future time points. The desired changes may be received upfront or on a real time basis (i.e. at time points substantially close to when the changes are desired). In some implementations, there can be a plurality of target drug delivery profiles corresponding to different future time points. The initial target drug delivery profile can be represented as $dd_{target0}$, and the subsequent target drug delivery profiles can be represented as $dd_{target1}$, $dd_{target2}$, etc.

Operations also include determining (430) initial parameters related to the drug flow and carrier fluid flow. For example, determining the initial parameters can include calculating an initial drug concentration and the proportionality factor p between the carrier and drug flows. In some implementations, the initial state is the steady state, that is, the drug and carrier fluids have previously been running long enough to achieve some steady state drug delivery. Determining the initial parameters can also include calculating the initial drug delivery profile that, for example, can be calculated as:

$$dd_{target0} = Q_{d0} * c_d \quad (19)$$

In some implementations, the initial parameters can also include the total flow rate at the initial state, which can be calculated as the sum of the flow rates for the drug and the carrier fluid, as:

$$Q_{T0} = Q_{c0} + Q_{d0} \quad (20)$$

The mixed drug concentration at the initial state can also be calculated, for example, as:

$$c_{ss} = (Q_{d0}/Q_{T0}) * c_d \quad (21)$$

The proportionality can be calculated, for example, as:

$$p = Q_{c0}/Q_{d0} \quad (22)$$

Operations also include receiving (440) receiving new target delivery profile. The new target delivery profile can be retrieved from a pre-loaded list (e.g. provided by a user with the dosage information) or received on a real time basis. In some implementations, new target delivery profiles can be retrieved from the pre-loaded list at pre-set time points.

Operations further include determining (450) new flow rates to conform to the new target delivery profile. The new flow rates can then be used by a computing device to adjust the infusion pumps at particular time points corresponding to the delivery profile changes. For example, the new flow rates corresponding to the delivery profile $dd_{target1}$ can be used to adjust the infusion pumps such that the delivery profile dd $dd_{target1}$ goes into effect a particular time $t_1$. In some implementations, the new flow rates are determined ahead of the particular time points. In some implementations, calculating the new flow rates is based on maintaining the steady state drug concentration $c_{ss}$ constant by keeping the proportionality factor p unchanged. In some implementations, the new total flow rate $Q_{T1}$ can be calculated as:

$$Q_{T1} = dd_{target1}/c_{ss} \quad (23)$$

The new drug flow can be calculated, for example, as:

$$Q_{d1} = Q_{T1}/(1+p) \quad (24)$$

The new carrier flow can be calculated, for example, as a difference between the new total flow and the new drug flow as:

$$Q_{c1} = Q_{T1} - Q_{d1} \quad (25)$$

Existing flow rates can then be replaced with the calculated new flow rates such that the new delivery profile goes into effect at a particular time point. Operations also include maintaining (460) the new flow rates until a time point (e.g., T2) when the next delivery profile change takes place. In some implementations, the operation 440 is repeated at T2 for a corresponding drug delivery profile $dd_{target2}$, and possibly a new total flow $Q_{T2}$. In some implementations, the mixed drug concentration $c_{ss}$ and the proportionality factor p is unchanged for the new drug delivery profile $dd_{target1}$.

Maintenance of Steady State

In some implementations, after a target drug delivery profile has been achieved, there may be a period of time during which the drug and the carrier flows are maintained at particular levels and no substantial changes are anticipated for a period of time. In some implementations, the methods and systems described herein can be used to minimize the amount of carrier fluid that is delivered to the target. This can be done, for example, by slowly ramping down the carrier fluid flow rate to a specified target flow rate during the maintenance phase. The rate of decrease in the carrier fluid flow can be chosen based on the model to keep drug delivery substantially within a particular range around the target delivery rate. The particular range can be chosen, for example, by a clinician. In some implementations, as the carrier fluid flow rate is gradually adjusted downward, the drug concentration slowly increases along the fluid path. In such cases, the target carrier fluid flow can be achieved over a period of time, thereby allowing optimization of total fluid delivery. The model can be used to track the calculated concentration of drug along the fluid path. In some cases, if a drug delivery change becomes necessary at any point during the maintenance phase (either during ramping down the carrier fluid rate or after the target carrier flow has been achieved), such a change can be made as described in the previous section to achieve a new desired target drug delivery profile.

Drug Cessation Phase

In general cessation of drug delivery can be achieved substantially similarly to a decrease in drug delivery. In some implementations, the proportionality p between the carrier and drug flows is gradually changed during the drug cessation phase. This allows a typically small carrier flow to be maintained during the cessation phase, for example, to keep venous access to the patient and deliver drug within the dead volume at a negligible rate of delivery to the patient. In some implementations, the model allows for calculation of the remaining concentration of drug along the fluid path during this "washout" period. If, for some reason, the carrier and/or the drug flow are turned up during this time, such calculation accounts for the remaining drug along the fluid path and ensures that an undesirable bolus of drug is not delivered at the target.

Controlling Multiple Drugs and Carriers

Even though the above applications have been generally described with reference to only one drug flow and one carrier fluid flow, a higher number of flows can be controlled without deviating from the scope of the present disclosure. In some implementations, multiple drugs can be delivered through the same fluid path using a single carrier fluid flow. In some implementations, an appropriate data repository, for example a multi-drug electronic library, can provide guidance as to which drugs can be safely delivered together through the same fluid path. The data repository, such as the multi-drug electronic library, can be accessed by the computing device controlling the infusion pumps to achieve safe delivery profiles. In case non-compatible drugs (e.g. drugs that may react with one another to produce harmful substances or drugs that may reduce the efficacy of one another) are attempted to be delivered together, the computing device can be configured to trigger an alarm or otherwise stall the attempted delivery based on information from the data repository.

In addition to identifying these types of drug-drug interactions, in some implementations, when two or more drugs are delivered over a fluid path with a single carrier fluid, each drug may be assigned a "criticality" based on clinical parameters. Criticality ratings may in some implementations be related to drug half-life and potency (e.g. degree of ability to change hemodynamic parameters for a given dose of vasoactive drug) as well as biological target, among other factors. Allowable variances for each drug may be assigned, providing the ability to control delivery of a given drug while maintaining delivery levels of the other drugs infused via the same line within safe and therapeutically desirable ranges. The allowable variances for individual drugs, as well as the "criticality" ratings, may in some implementations be incorporated into a new, extended version of the multi-drug library (data repository mentioned above).

When multiple drugs are delivered together, e.g., to the same patient, in some implementations the drugs can be mixed together in appropriate amounts and dispensed from a single drug infusion pump. In some implementations, each of the multiple drugs can be dispensed from a separate drug infusion pump and mixed together at a flow junction structure such as a manifold. In such cases, each of the multiple drug infusion pumps as well as the carrier fluid infusion pump can be controlled in the coordinated way as described above. For example, the model can be used to calculate concentrations of each of the drugs along the fluid path at any moment in time. The model can also be used to calculate the delivery profile of each drug at the delivery point. For each drug, all of the other drug flows combined with the carrier flow can be treated as a single combined carrier flow, and the model can be applied to predict delivery profile of each drug. In some implementations, these predictions can also serve as the basis for visualizations as described for the single drug plus carrier case in this document.

To enhance control of delivery of multiple drugs from multiple drug infusion pumps via a single fluid path (as described above), in some implementations, depending on criticality and allowable variance, individual drugs could be assigned to appropriate ports on a flow junction structure such as a manifold. This process of assignment may make use of parameters such as dead volume or empirical dead volume retrieved from an electronic library of catheter or infusion set parameters. For example, a drug with high criticality may be assigned to (recommended to be administered via) the manifold port that has the smallest dead volume of available ports.

In some implementations, various algorithms can be used to ensure optimization of delivery for each individual drug and for the drugs in combination. In addition to the assignment of drugs to manifold ports based on criticality, allowable variances, and catheter/infusion set parameters, the algorithms can, in some implementations, be designed to maintain each drug within its allowable variance as changes to other drugs are made. For multiple drugs delivered through a single fluid path, in some cases, it may not be possible to maintain all drugs at desired levels deterministically when changes are made to a subset of those drugs. In these cases, some implementations may involve constrained optimization, where some degree of drift within allowable variances is allowed for each drug, with the goal of maintaining tighter tolerances for more critical drugs while still keeping less critical drugs within safe and efficacious ranges.

As an example of such control, consider a case where four drugs are delivered via a four port manifold. The four drugs join with a carrier fluid and are transmitted as mixed fluid via a single fluid path. Suppose that it is desired to double the dose of the most critical drug (say, drug 1) at a given time. Using previously described algorithms, the flow of drug 1 can be doubled and the carrier flow can also be raised so as to maintain the concentration of drug 1 in the fluid path. If the flows of drug 2, drug 3, and drug 4 are kept constant, the techniques described previously can be used to calculate the temporary increases in delivery of drugs 2, 3, and 4 as the masses of those drugs already in the fluid path are moved more quickly (due to the higher flow) into the patient. If the peak levels of those less critical drugs stays within their allowable variances, this provides a solution to quickly and accurately altering the delivery of the most critical drug. Flows may be further adjusted after the initial change to minimize excess volume delivery, using the algorithms previously described.

To extend this example, in the case where the second most critical drug (call it drug 2) would move outside its allowable range using the above method of changing drug 1 dosing, the flow of drug 2 (and/or drug 3, drug 4, and the carrier fluid) can be altered so that drug 1 still comes quickly to target levels, but allows drug 2 to stay within allowable levels. This enters the realm of constrained optimization previously mentioned. In some implementations, drug 1 could also be allowed to vary within specified tolerances to enable this type of optimization.

As a second example of multi-drug control, consider the case where rapid initiation (rapid onset) of all four drugs (for the four drug plus carrier architecture described above) is desired. In such a case, the rapid onset algorithm previously described for a single drug plus carrier also applies. Each of the four drug flows and the carrier flow would initially be set to a high level, initially setting carrier flow to the maximum allowable rate and setting each drug fluid flow at a rate that achieves a drug concentration in the fluid path equal to what the drug concentration will be when the carrier and drug flow are reduced to steady state levels. After models, such as those previously described, have determined that the most critical drug has reached the target drug delivery rate, alterations of the drug flows (for each of the four concurrently delivered drugs) and carrier flow can be made in parallel, keeping the ratio of drug flow to mixed fluid flow at a constant value for each of the drugs.

The methods and examples described here are equally valid for manifolds where dead volumes differ between access points (e.g. linear manifolds) as well as manifolds where there is little or no difference in the dead volumes for the different access points (e.g. manifolds with access ports aligned in radial fashion or in parallel orientation).

In some implementations, the methods and systems described herein allow users to account for changes introduced by the concurrent use of multiple pumps. For example, the multiple infusion pumps can be integrated as part of an overall system, a coordinated control of which allows more precise control of administration of multiple drugs, for example, at points of transition in therapies.

Examples of Use

In some implementations, the methods and systems described herein can be used in an "assist" mode," where the software uses the model to give guidance in achieving a target drug delivery profile. In such a case, a clinician may manually manipulate the parameters for the infusion pumps. Alternatively, in a "control" mode, the software can be configured to make recommended changes in pump settings for clinician approval. In some implementations, the system may operate in a "visualization" mode, where the system is used primarily to display predicted drug delivery based on values the clinician has chosen. In this mode, the clinician operates the infusion pumps, and the system monitors what the pumps are doing. Even in the "visualization" mode, however, visual and audible warnings as well as the ability to see a graphical display of predicted drug delivery can facilitate informed decision-making. Providing user guidance in the form of warnings, recommendations, or direct changes to pump settings can be important in cases involving coordination of multiple pumps as part of the overall clinical management using the system.

For decision support and for teaching purposes, the system may also operate in a "predictive" mode. In this predictive mode, clinicians or learners can enter different choices of infusion tubing, manifolds, or vascular access catheters into the software, along with the pump settings. They can then view the resulting predictions for drug delivery profiles, and explore various hypothetical scenarios without actually administering medication. This exploits the capabilities of the system as a tool for teaching.

In some implementations, at least portions of the system could be incorporated into integrated chips, and could therefore be integrated with other electronic devices such as the infusion pumps. The ability of the system to run on laptops, tablet PCs, and other portable devices, can enhance portability, thereby extending use of the system to various clinical situations including, for example, critical care at an emergency scene. Portability can also facilitate safe management of infusion therapy, when, for example, a patient travels from an intensive care unit (ICU) to an operating room (OR) or to a radiology suite, or from an emergency room (ER) to the ICU, OR, etc.

In some implementations, at least a portion of the pump-control system can be embedded in the microprocessor control mechanisms of the infusion pump itself. Such an infusion pump can serve as a standalone unit for delivering a drug, without integration with the output of other pumps.

In some implementations, the methods and systems described herein can be used in the delivery of Total Intravenous Anesthesia (TIVA) for patients requiring surgery. Traditional anesthesia delivery systems have required the capability to supply measured amounts of inhalation anesthetics (e.g., nitrous oxide, sevoflurane, etc.). However, with the development of short acting intravenous agents that have analgesic (e.g., remifentanil), sedative/hypnotic (e.g., propofol), and muscle relaxant properties (e.g., cisatracurium), it is possible to provide anesthesia entirely by intravenous infusion. In some implementations, the methods and systems described herein can be configured for field use, such as in a military or trauma/rescue situation, and in remote location situations such as aerospace medicine. The interface module, processing device (e.g. a rugged laptop or tablet PC), and a small number of infusion pumps, syringes and tubing could be transported in a small container (e.g., a backpack) of limited weight and bulk, yet provide the ability to control the delivery of combinations of anesthetic agents by intravenous infusion in various environments.

In some implementations, the methods and systems described herein allow precise control of drug and fluid delivery in settings where the volumes of fluid must be limited for clinical reasons. For example, an infant or a small child undergoing surgery or treatment in an ICU or OR may not tolerate large volumes of fluid. Critically ill adult patients or adult patients with advanced medical conditions (e.g., kidney failure) may also be intolerant of large volumes of fluid administered in the course of treatment with infused medications. In such cases, precisely controlled (time and dose) infusions of sedative, analgesic, anesthetic, cardiac, or vasoactive medications may be delivered using the methods and systems described herein.

Overview of a Computing Device

Figure 5:
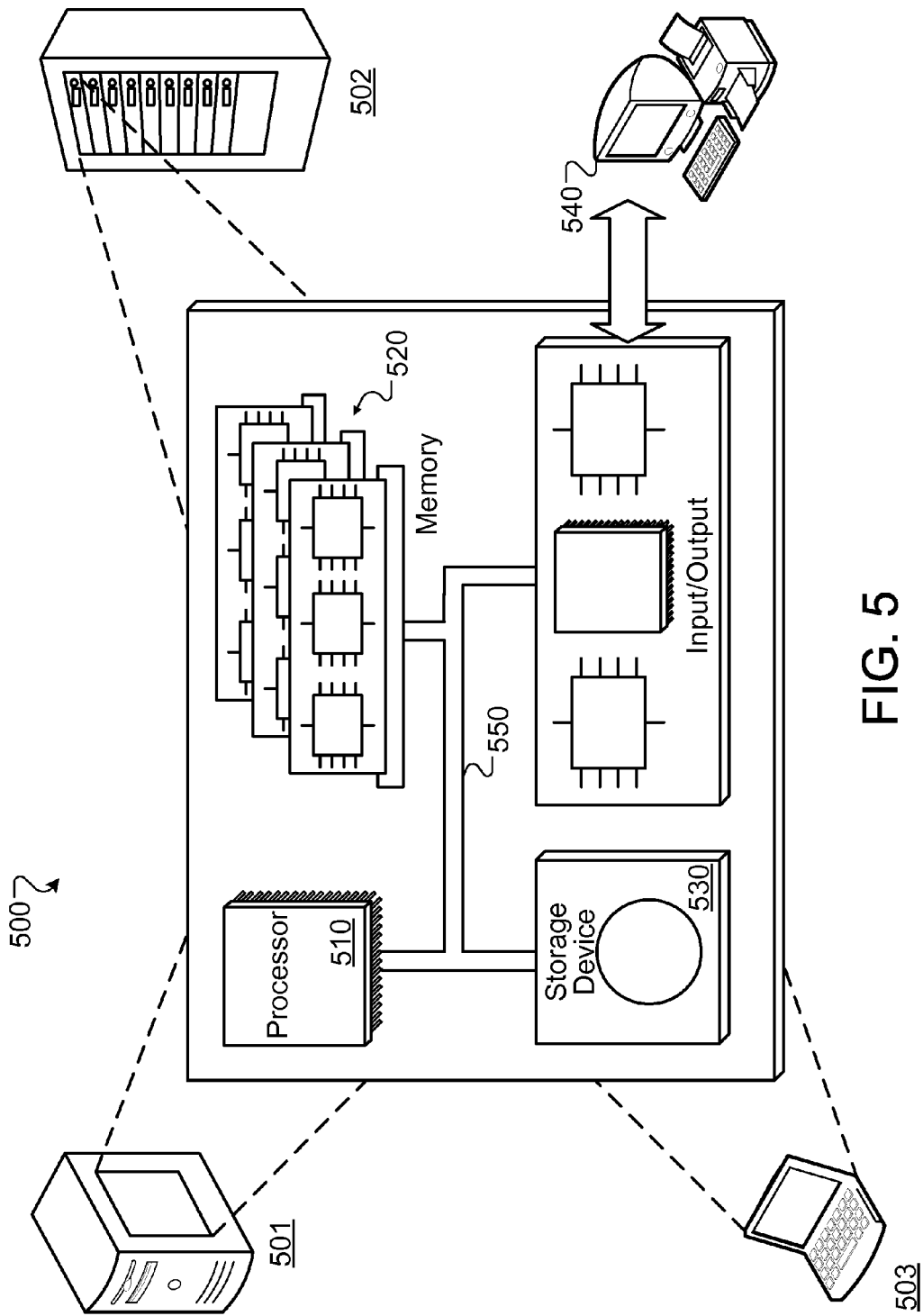
FIG. 5 is a schematic diagram of a computer system.

FIG. 5 is a schematic diagram of a computer system 500. The system 500 can be used for the operations described in association with any of the computer-implemented methods described herein, according to one implementation. The system 500 can be incorporated in various computing devices such as a desktop computer 501, server 502, and/or a laptop computer 503. The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In some implementations, the memory 520 is a computer-readable medium. The memory 520 can include volatile memory and/or non-volatile memory.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In some implementations, the input/output device 540 includes a keyboard and/or pointing device. In some implementations, the input/output device 540 includes a display unit for displaying graphical user interfaces. In some implementations the input/output device can be configured to accept verbal (e.g. spoken) inputs. For example, the clinician can provide the input by speaking into the input device.

The features described can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 510 carries out instructions related to a computer program. The processor 510 may include hardware such as logic gates, adders, multipliers and counters. The processor 510 may further include a separate arithmetic logic unit (ALU) that performs arithmetic and logical operations.

EXAMPLES

The methods and systems described herein are further illustrated using the following results, which do not limit the scope of the invention described in the claims.

Example 1

Reduction in Drug Delivery Onset Delay

Figure 6A:
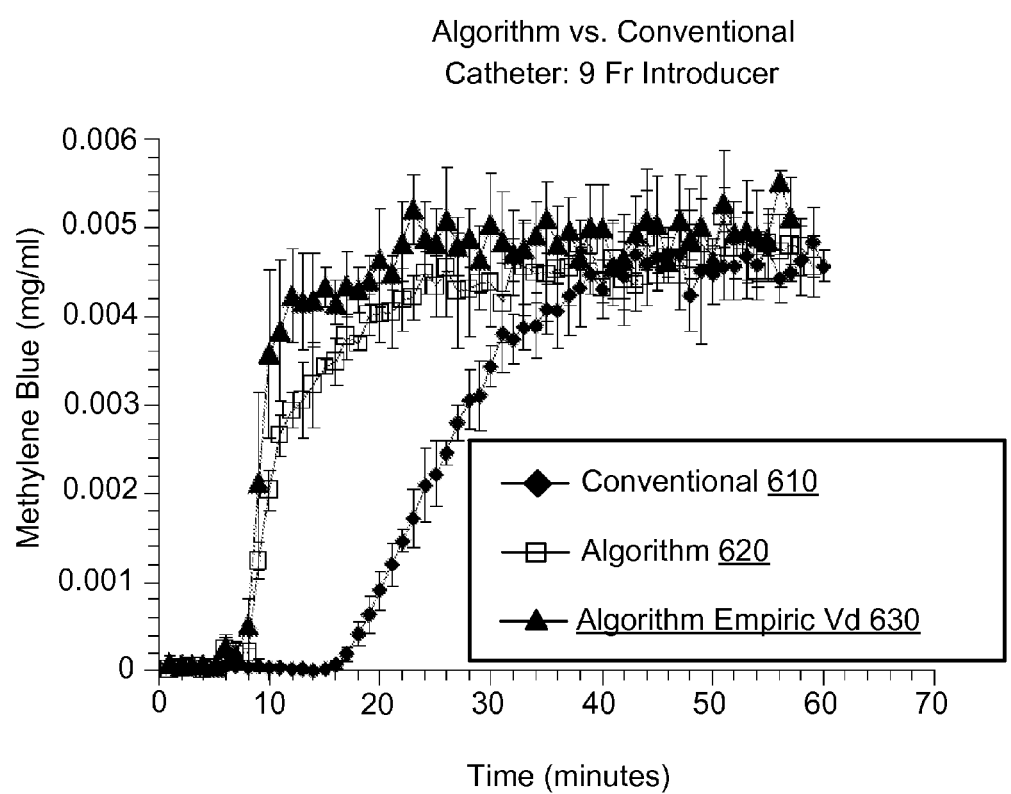
FIGS. 6A-6C are a set of plots that illustrate reduction in examples of drug delivery onset delay.

FIG. 6A shows a set of example plots that illustrate the reduction in drug delivery onset delay due to using the methods and systems described herein. The plots represent the concentration of drug (in mg/ml) at the delivery point as functions of time. In this experiment, the infusion pump for the drug was switched on at the 6 minute mark. Methylene Blue was used as the drug. An adult sized catheter (9 Fr Introducer) was used for these experiments. The flow junction structure was a linear stopcock manifold where the drug entered the fluid path at a third position along the manifold. The plot 610 (referred to as "Conventional") represents the case where no algorithms were used to control the drug and carrier flows which were kept constant at 3 ml/hour and 10 ml/hour, respectively. The plot 620 (referred to as "Algorithm") represents the case where the model described above was used to control the drug and carrier fluid pumps using a measured dead volume. The plot 630 (referred to as "Algorithm Empiric Vd") represents the case where the model described above was used to control the drug and carrier fluid pumps using an empirical dead volume. The predicted steady state rate of drug delivery was 0.005 mg/ml or 0.005 mg/min. As seen from the plot 610, without using the algorithmic controls described herein, the time of onset of the steady state is about 50 minutes. However, the onset delay was reduced significantly by using the model in conjunction with a measured dead volume (as seen from the plot 620) or an empirical dead volume (as seen from the plot 630).

Figure 6B:
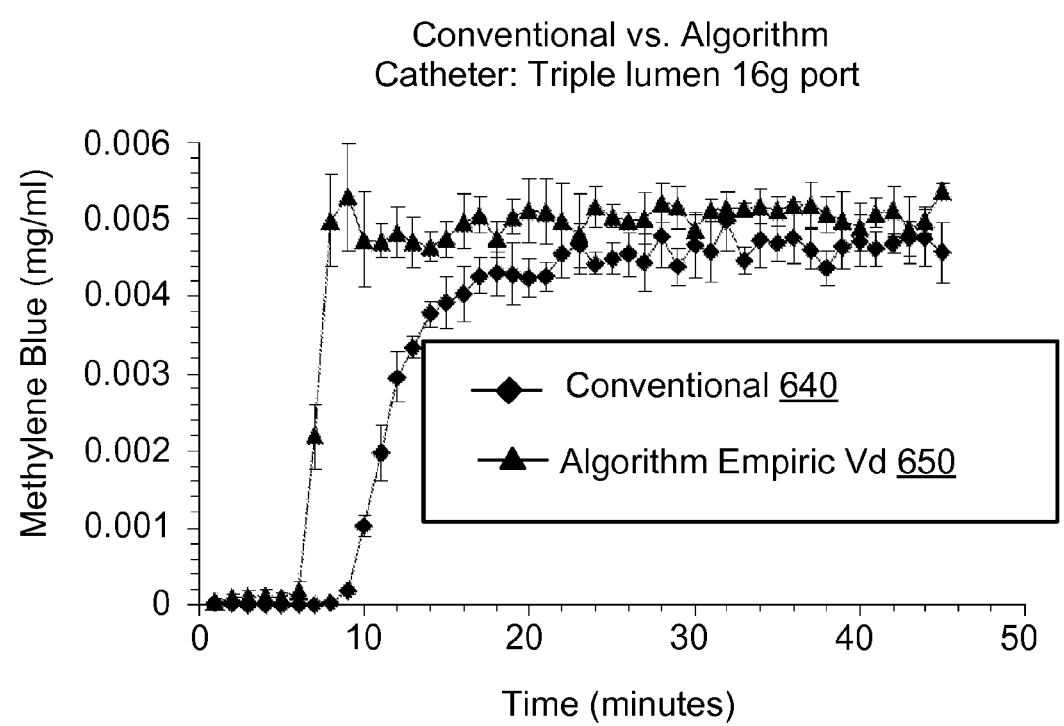

FIG. 6B shows another set of example plots that illustrate the reduction in drug delivery onset delay due to using the methods and systems described herein. In this case, the catheter used was a 16 g lumen of triple lumen central venous line. All other parameters were substantially the same as the corresponding parameters of the experiment described in FIG. 6A. The plot 640 (referred to as "Conventional") represents the case where no algorithms were used to control the drug and carrier flows. The plot 650 (referred to as "Algorithm Empiric Vd") represents the case where the model described above was used to control the drug and carrier fluid pumps using an empirical dead volume. Comparing the plots 640 and 650, it can be seen that the onset delay is significantly reduced on controlling the carrier and drug flows using the methods and systems described herein.

Figure 6C:
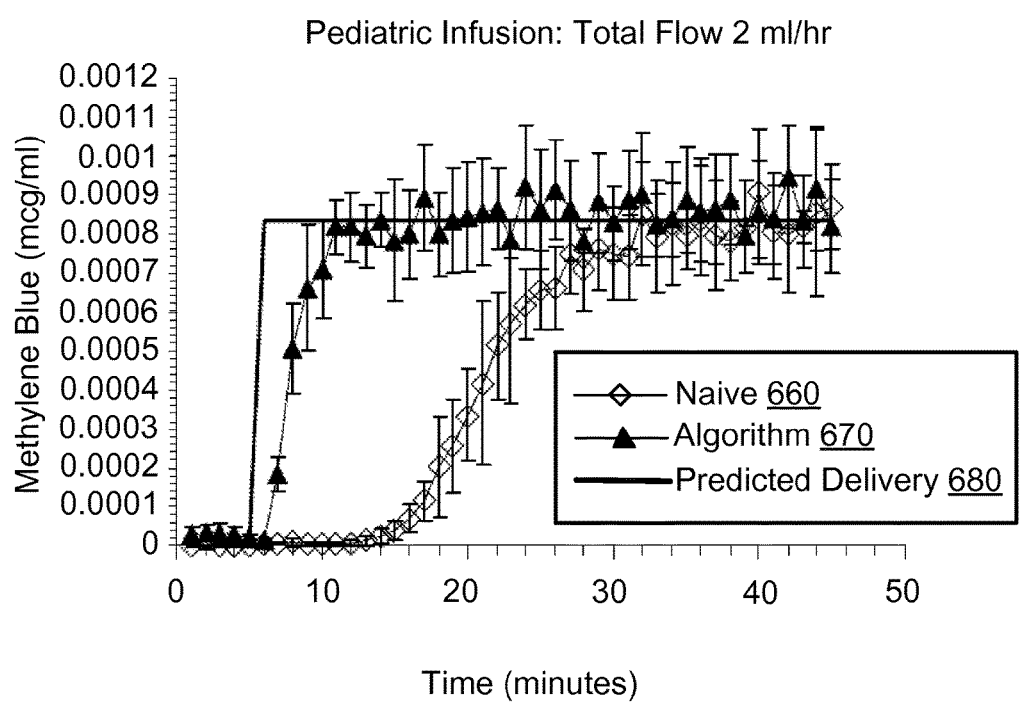

FIG. 6C shows another set of example plots that illustrate the reduction in drug delivery onset delay due to using the methods and systems described herein. In this case, a 4Fr pediatric central venous line catheter was used. The flow junction structure was a stopcock gang manifold where the drug entered the fluid path at a first position along the manifold. The drug used was Methylene Blue and the corresponding infusion pump was switched on at the 6 minute mark. The plot 660 (referred to as "Naive") represents the case where no algorithms were used to control the drug and carrier flows which were kept constant at 0.5 ml/hour and 1.5 ml/hour, respectively. The plot 670 (referred to as "Algorithm") represents the case where the model described above was used to control the drug and carrier fluid pumps using a measured dead volume. The plot 680 (referred to as "Predicted Delivery") represents the predicted steady state rate of drug delivery that was fixed at 0.00085 mg/ml. Comparing the plots 660 and 670, it can be seen that the onset delay is significantly reduced on controlling the carrier and drug flows using the methods and systems described herein.

Example 2

Control of Drug Delivery Profiles

Figure 7:
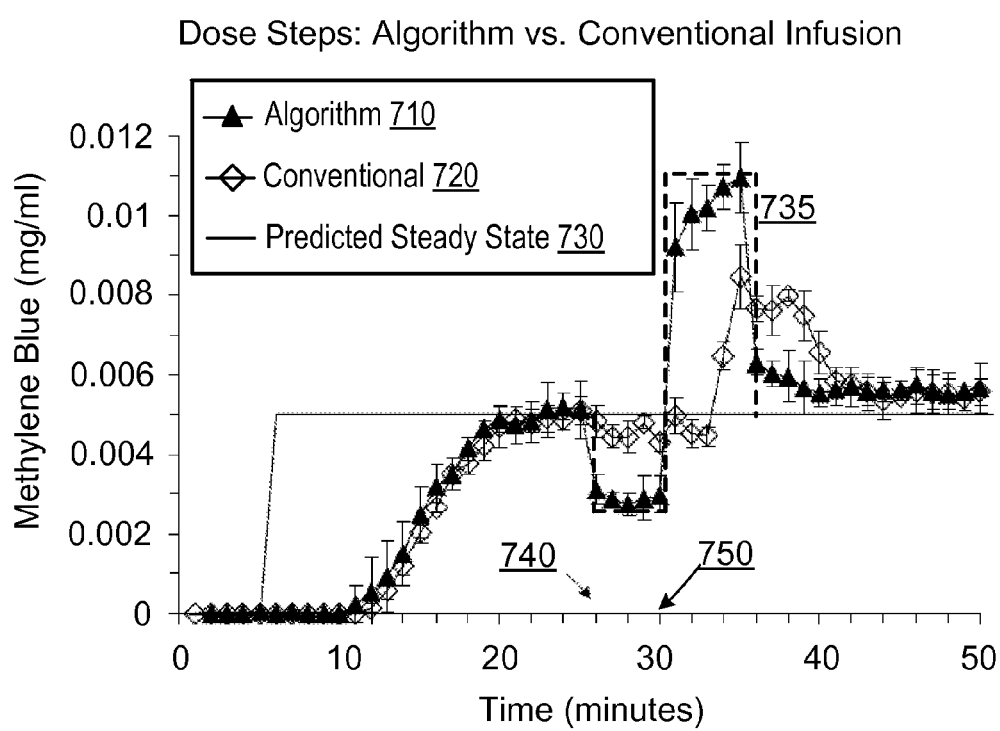
FIG. 7 is a set of plots that illustrate improved control over examples of drug delivery profiles.

FIG. 7 shows a set of example plots that illustrate the improved control of drug delivery profiles achieved using the methods and systems described herein. The plots represent the concentration of drug (in mg/ml) at the delivery point as functions of time for an adult subject. In this experiment, rapid step changes were made from the steady state (represented as the plot "predicted Steady State" 730) with and without using the algorithmic control of the infusion pumps. The ideal or intended step changes are represented by the broken line 735. As indicated by the broken line 735, the drug pump settings were halved from the steady state value at about the time point 740 and doubled from the steady state value at about the time point 750. The infusion pump for the drug was switched on at the 6 minute mark. Methylene Blue was used as the drug. The catheter used was a 16 g lumen of triple lumen central venous line. The flow junction structure was a stopcock gang manifold where the drug entered the fluid path at a third position along the manifold. The plot 720 (referred to as "Conventional") represents the case where no algorithm was used to control the drug and carrier flows which were kept constant at 3 ml/hour and 10 ml/hour, respectively. The plot 710 (referred to as "Algorithm") represents the case where the model described above was used to control the drug and carrier fluid pumps using a measured dead volume. The predicted steady state rate (plot 730) of drug delivery was 0.005 mg/ml or 0.005 mg/min. Comparing the plots 710 and 720, it can be seen that the rapid changes can be controlled much better using the methods and systems described herein.

Other Embodiments

It is to be understood that while the invention has been described in conjunction with the detailed description thereof the foregoing description is intended to illustrate and not limit the scope of the invention, which is defined by the scope of the appended claims. For example, the methods and systems described herein can be used for controlling pumps other than infusion pumps. Other aspects, advantages, and modifications are within the scope of the following claims.

What is claimed is:

1. A system for controlling a drug delivery profile, the system comprising:
   at least one drug pump that produces a drug flow, wherein the at least one drug pump dispenses at least a first drug;
   at least one carrier fluid pump that produces a carrier fluid flow;
   a flow junction structure configured to receive the drug flow and the carrier fluid flow to produce a mixed flow delivered to a delivery point;
   a fluid path for carrying the mixed flow between the flow junction structure and the delivery point, at least a portion of the fluid path being represented by a dead volume;
   a first controllable valve disposed between the at least one drug pump and the flow junction structure;
   a second controllable valve disposed between the at least one carrier fluid pump and the flow junction structure; and
   a control module configured to control a drug delivery profile at the delivery point in accordance with a target drug delivery profile and a predictive model of the mixed flow,
   wherein the control module is configured to vary a drug flow rate by controlling the first controllable valve, and vary a carrier fluid flow rate by controlling the second controllable valve,
   wherein each of the drug flow rate and the carrier fluid flow rate is varied relative to corresponding target rates associated with the target drug delivery profile such that an initial drug flow rate and an initial carrier fluid flow rate are higher than the corresponding target rates while a ratio between the drug flow rate and the carrier fluid flow rate is substantially fixed in accordance with a target drug concentration in the mixed flow corresponding to the target drug delivery profile, and
   wherein the predictive model is usable for predicting variations in the drug concentration along the fluid path, the predictive model being based on a plurality of structural parameters related to propagation of the mixed flow through the fluid path, the structural parameters including the dead volume associated with the fluid path.

2. The system of claim 1, further comprising a first constant pressure valve and a second constant pressure valve disposed upstream from each of the first and second controllable valves, respectively, wherein each of the first and second constant pressure valves is configured to maintain a constant pressure upstream of a corresponding controllable valve for a fluid that flows through the corresponding controllable valve.

3. The system of claim 1, wherein the control module is further configured to adjust a drug delivery rate at the delivery point by simultaneously controlling the drug flow rate and the carrier fluid flow rate while the ratio of the drug flow rate and the carrier fluid flow rate is substantially fixed.

4. The system of claim 1, wherein a drug concentration in the drug flow is substantially fixed while the ratio between the drug flow rate and the carrier fluid flow rate is substantially fixed.

5. The system of claim 1, wherein the control module adjusts the drug flow rate to achieve a predicted drug delivery rate calculated using at least the predictive model of the mixed flow.

6. The system of claim 1, wherein the control module is further configured to adjust the drug delivery profile such that excess volume delivery over time is substantially reduced while maintaining target drug delivery within allowable tolerances.

7. The system of claim 1, wherein the control module is further configured to vary the drug flow rate and the carrier fluid flow rate relative to the corresponding target rates by:
   setting the initial drug flow rate and the initial carrier fluid flow rate at substantially high values within corresponding allowable ranges; and
   reducing, after a predetermined amount of time has elapsed, the drug flow rate and the carrier fluid flow rate such that the drug delivery profile at the delivery point substantially corresponds to the target drug delivery profile.

8. The system of claim 7, wherein the predetermined amount of time is substantially equal to a time taken by the mixed flow to traverse the fluid path when the drug flow rate and the carrier fluid flow rate are set at the initial drug flow rate and the initial carrier fluid flow rate, respectively.

9. The system of claim 1, wherein the control module is configured to trigger an alarm upon detecting that at least one of the drug flow rate, the carrier fluid flow rate, and the drug delivery profile is outside a corresponding pre-defined range associated with the drug.

10. The system of claim 1, wherein the control module is configured to control the drug delivery profile at the delivery point by
   setting the drug flow rate and the carrier fluid flow rate to target rates corresponding to a first target drug delivery profile; and
   in response to receiving a signal indicative of a second target drug delivery profile, adjusting the drug flow rate and the carrier fluid flow rate relative to target rates corresponding to the second target drug delivery profile while the ratio of the drug flow rate and the carrier fluid flow rate is substantially fixed in accordance to a second target drug concentration in the mixed flow corresponding to the second target drug delivery profile.

11. A system for controlling a drug delivery profile, the system comprising:
a first controllable valve that controls a drug flow;
a second controllable valve that controls a carrier fluid flow;
a flow junction structure configured to receive the drug flow and the carrier fluid flow to produce a mixed flow delivered to a delivery point;
a fluid path for carrying the mixed flow between the flow junction structure and the delivery point, at least a portion of the fluid path being represented by a dead volume; and
a control module configured to control a drug delivery profile at the delivery point in accordance with a target drug delivery profile and with a predictive model of the mixed flow,
wherein the control module is configured to vary a drug flow rate by controlling the first controllable valve, and vary a carrier fluid flow rate by controlling the second controllable valve,
wherein each of the drug flow rate and the carrier flow rate is varied relative to corresponding target rates associated with the target drug delivery profile such that an initial drug flow rate and an initial carrier fluid flow rate are higher than the corresponding target rates while a ratio between the drug flow rate and the carrier fluid flow rate is substantially fixed in accordance with a target drug concentration in the mixed flow corresponding to the target drug delivery profile, and
wherein the predictive model is usable for predicting variations in the drug concentration along the fluid path, the predictive model being based on a plurality of structural parameters related to propagation of the mixed flow through the fluid path, the structural parameters including the dead volume associated with the fluid path.

12. The system of claim 11, wherein the control module is configured to trigger an alarm upon detecting that at least one of the drug flow rate, the carrier fluid flow rate, and the drug delivery profile is outside a corresponding pre-defined range associated with the drug.

13. The system of claim 11, wherein the control module is configured to control the drug delivery profile at the delivery point by
setting the drug flow rate and the carrier fluid flow rate to target rates corresponding to a first target drug delivery profile; and
in response to receiving a signal indicative of a second target drug delivery profile, adjusting the drug flow rate and the carrier fluid flow rate relative to target rates corresponding to the second target drug delivery profile while the ratio of the drug flow rate and the carrier fluid flow rate is substantially fixed in accordance to a second target drug concentration in the mixed flow corresponding to the second target drug delivery profile.

* * * * *